US011794184B2

(12) United States Patent
Hou et al.

(10) Patent No.: US 11,794,184 B2
(45) Date of Patent: Oct. 24, 2023

(54) THREE-DIMENSIONAL (3D) HYDROGEL PATTERNING IN MICROFLUIDIC VASCULAR MODELS

(71) Applicant: NANYANG TECHNOLOGICAL UNIVERSITY, Singapore (SG)

(72) Inventors: Han Wei Hou, Singapore (SG); Nishanth Venugopal Menon, Singapore (SG); Soon Nan Wee, Singapore (SG); King Ho Holden Li, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 1084 days.

(21) Appl. No.: 16/336,784

(22) PCT Filed: Sep. 29, 2017

(86) PCT No.: PCT/SG2017/050491
§ 371 (c)(1),
(2) Date: Mar. 26, 2019

(87) PCT Pub. No.: WO2018/063099
PCT Pub. Date: Apr. 5, 2018

(65) Prior Publication Data
US 2019/0217291 A1    Jul. 18, 2019

(30) Foreign Application Priority Data

Sep. 29, 2016  (SG) .......................... 10201608126Q

(51) Int. Cl.
*B01L 3/00*  (2006.01)
*C12M 3/00*  (2006.01)
(Continued)

(52) U.S. Cl.
CPC ......... *B01L 3/502707* (2013.01); *C12M 3/00* (2013.01); *C12M 21/08* (2013.01);
(Continued)

(58) Field of Classification Search
CPC . B01L 3/502707; B01L 2200/12; C12M 3/00; C12M 21/08; C12M 23/16;
(Continued)

(56) References Cited

U.S. PATENT DOCUMENTS

2009/0035793 A1    2/2009 Nishino et al.
2014/0065034 A1    3/2014 Zheng et al.
(Continued)

FOREIGN PATENT DOCUMENTS

| JP | 2009-505634 A | 2/2009 |
| JP | 2014-530635 A | 11/2014 |
| KR | 10-1597210 B1 | 2/2016 |

OTHER PUBLICATIONS

Gumuscu et al. "Large scale patterning of hydrogel microarrays using capillary pinning." Lab on a Chip. vol. 15, pp. 664-667. 2015 (Year: 2015).*

(Continued)

*Primary Examiner* — Michael L Hobbs
(74) *Attorney, Agent, or Firm* — SEED IP LAW GROUP LLP

(57) ABSTRACT

The present disclosure provides a device for patterning extracellular matrix (ECM) hydrogel comprising a first layer surface patterned to define a microchannel, a second layer comprising a loading channel in fluid communication with loading ports to receive an ECM hydrogel, wherein the first layer is attached over the second layer such that the patterned surface faces the loading channel to define an open chamber with regions of reduced cross-sectional area, and wherein the ECM hydrogel is confined to fill said regions, (Continued)

thereby forming a perfusable channel in the open chamber. The present disclosure also provides the same device wherein the second layer is a substrate without a loading channel and is optically pervious; and additionally provides a method of patterning ECM hydrogel comprising use of the aforementioned device. Importantly, ECM patterning is achieved by surface tension between the ECM hydrogel and the first layer at the boundaries of the microchannel.

20 Claims, 14 Drawing Sheets

(51) Int. Cl.
  C12M 1/00 (2006.01)
  C12M 3/06 (2006.01)
  G01N 33/50 (2006.01)
  C12M 1/12 (2006.01)
(52) U.S. Cl.
  CPC ............ *C12M 23/16* (2013.01); *C12M 23/20* (2013.01); *C12M 29/10* (2013.01); *G01N 33/5064* (2013.01); *G01N 33/5082* (2013.01); *B01L 2200/12* (2013.01); *C12M 25/14* (2013.01)
(58) Field of Classification Search
  CPC ...... C12M 23/20; C12M 29/10; C12M 25/14; G01N 33/5064; G01N 33/5082
  See application file for complete search history.

(56) References Cited

U.S. PATENT DOCUMENTS

| | | | |
|---|---|---|---|
| 2014/0302594 A1 | 10/2014 | Chung et al. | |
| 2016/0139110 A1* | 5/2016 | Zantl | G01N 33/5029 435/287.1 |
| 2017/0130187 A1* | 5/2017 | Lee | B01L 3/502738 |

OTHER PUBLICATIONS

Office Action (w/ English Translation), dated Nov. 9, 2021, for Japanese Application No. 2019-516971. (8 pages).
Alba-Loureiro et al., "Neutrophil function and metabolism in individuals with diabetes mellitus," *Brazilian Journal of Medical and Biological Research*, 40:1037-1044, 2007.
Baker et al., "Microfluidics embedded within extracellular matrix to define vascular architectures and pattern diffusive gradients," *Lab Chip*, 13:3246-3252, 2013.
Bergers et al., "The role of pericytes in blood-vessel formation and maintenance," *Neuro-Oncology*, 7:452-464, 2005.
Bischel et al., "Tubeless microfluidic angiogenesis assay with three-dimensional endothelial-lined microvessels," *Biomaterials*, 34:1471-1477, 2013.
Bischel et al., "A Practical Method for Patterning Lumens through ECM Hydrogels via Viscous Finger Patterning," *Journal of Laboratory Automation*, 17(2): 96-103, 2012.
Chandrasekharan et al., "Tumor necrosis factor α (TNF-α) receptor-II is required for TNF-α-induced leukocyte-endothelial interaction in vivo," *Blood*, 109(5):1938-1944, 2007, (8 pages).
Cho et al., "How the capillary burst microvalve works," *Journal of Colloid and Interface Science*, 306:379-385, 2007.
Chrobak et al., "Formation of perfused, functional microvascular tubes in vitro," *Microvascular Research*, 71:185-196, 2006.
Chung et al., "Cell migration into scaffolds under co-culture conditions in a microfluidic platform," *Lab Chip*, 9:269-275, 2009.
Gumuscu et al., "Large scale patterning of hydrogel microarrays using capillary pinning," *Lab Chip*, 15:664-667, 2015.
Hasan et al., "A multilayered microfluidic blood vessel-like structure," *Biomedical Microdevices*, 17(88):1-13, 2015.

Holme et al., "Shear-Induced Platelet Activation and Platelet Microparticle Formation at Blood Flow Conditions as in Arteries with a Severe Stenosis," *Arteriosclerosis, Thrombosis, and Vascular Biology*, 17:646-653, 1997, (23 pages).
Hou et al., "Rapid and label-free microfluidic neutrophil purification and phenotyping in diabetes mellitus," *Scientific Reports*, 6(29410):1-12, 2016.
Hsu et al., "A microfluidic platform for generating large-scale nearly identical human microphysiological vascularized tissue arrays," *Lab Chip*, 13:2990-2998, 2013.
Huang et al., "Engineering microscale cellular niches for three-dimensional multicellular co-cultures," *Lab Chip*, 9:1740-1748, 2009.
Huxley et al., "Quantitative fluorescence microscopy on single capillaries: alpha-lactalbumin transport," American Journal of Physiology, H188-H197, 1987, (10 pages).
Kang et al., "Capillarity Guided Patterning of Microliquids," *Small*, 11(23):2789-2797, 2015.
Kim et al., "Probing nanoparticle translocation across the permeable endothelium in experimental atherosclerosis," *PNAS*, 111(3):1078-1083, 2014.
Kim et al., "Engineering of functional, perfusable 3D microvascular networks on a chip," *Lab Chip*, 13:1489-1500, 2013.
Mannino et al., "Do-it-yourself in vitro vasculature that recapitulates in vivo geometries for investigating endothelial-blood cell interactions," *Scientific Reports*, 5(12401):1-13, 2015.
Menon et al., "A novel extracellular matrix (ECM) patterning technique for engineering biomimetic 3D microvasculature," Singapore National Research Foundation, 2 pages, 2017.
Menon et al., "Micro-engineered perfusable 3D vasculatures for cardiovascular diseases," *Lab Chip*, 17:2960-2968, 2017.
Patibandla et al., "Hyperglycemic Arterial Disturbed Flow Niche as an In Vitro Model of Atherosclerosis," *Analytical Chemistry*, 86:10948-10954, 2014.
Robert et al., "A Three-Dimensional Engineered Artery Model for In Vitro Atherosclerosis Research," *PLoS ONE*, 8(11): e79821, pp. 1-10, 2013.
Roberts et al., "Micropatterning and Assembly of 3D Microvessels," *Journal of Visualized Experiments*, 115(e54457):1-10, 2016.
Rouleau et al., "Neutrophil Adhesion on Endothelial Cells in a Novel Asymmetric Stenosis Model: Effect of Wall Shear Stress Gradients," *Annals of Biomedical Engineering*, 38(9):2791-2804, 2010.
Sato et al., "Microcirculation-on-a-Chip: A Microfluidic Platform for Assaying Blood- and Lymphatic-Vessel Permeability, " *PLoS ONE*, 10(9):e0137301, pp. 1-10, 2015.
Schoephoerster et al., "Effects of Local Geometry and Fluid Dynamics on Regional Platelet Deposition on Artificial Surfaces," *Arteriosclerosis and Thrombosis*, 13(12):1806-1813, 1993. (9 pages).
Shin et al., "Microfluidic assay for simultaneous culture of multiple cell types on surfaces or within hydrogels," *Nature Protocols*, 7(7):1247-1259, 2012, (14 pages).
Srigunapalan et al., "A microfluidic membrane device to mimic critical components of the vascular microenvironment," *Biomicrofluidics*, 5(013409):1-9, 2011.
Takaku et al., "An In Vitro Coculture Model of Transmigrant Monocytes and Foam Cell Formation," *Arteriosclerosis, Thrombosis, and Vascular Biology*, 19:2330-2339, 1999, (11 pages).
van Duinen et al., "Microfluidic 3D cell culture: from tools to tissue models," *Current Opinion in Biotechnology*, 35:118-126, 2015.
Zervantonakis et al., "Three-dimensional microfluidic model for tumor cell intravasation and endothelial barrier function," *PNAS*, 109(34):13515-13520, 2012.
Zheng et al., "In vitro microvessels for the study of angioeenesis and thrombosis." *PNAS*, 109(24):9342-9347, 2012, (7 pages).
Gumuscu et al., "Large scale patterning of hydrogel microarrays using capillary pinning," *Lab Chip* 15:664-661, 2015, (13 pages).
Office Action (w/ English Translation), dated Jul. 20, 2021, for Japanese Application No. 2019-516971, (14 pages).

* cited by examiner

THREE-DIMENSIONAL (3D) HYDROGEL PATTERNING IN MICROFLUIDIC VASCULAR MODELS

CROSS-REFERENCE TO RELATED APPLICATION

This application claims the benefit of priority of Singapore Patent Application No. 10201608126Q, filed 29 Sep. 2016, the content of it being hereby incorporated by reference in its entirety for all purposes.

TECHNICAL FIELD

The present disclosure relates to a device and a method for patterning extracellular matrix hydrogel.

BACKGROUND

Endothelial dysfunction is a pathophysiological hallmark in many diseases including diabetes, cardiovascular diseases and cancer. Most vascular research involved complicated animal models and in vivo imaging techniques, which impede characterization of hemodynamic and cell-cell interactions in blood vessel. Conventional in vitro vascular models tend to be based on Transwell assay and tissue engineering, which are likely limited by imaging difficulties with only endpoint studies possible. Microfluidics may be a valuable proposition over these conventional means for investigating cellular behavior in well-controlled microenvironment to understand biological phenomena that may be difficult to visualize and quantify in vivo. As two-dimensional (2D) microfluidic vascular models lack physiological relevance, biomimetic three-dimensional (3D) vascular platforms have been recently developed for angiogenesis, cancer metastasis and atherosclerosis. However, the channel designs in these "organ-on-a-chip" systems tend to be limited due to fabrication difficulties, and fail to reproduce important pathological vascular geometries such as bifurcation, stenosis or aneurysm.

Some of the conventional methods for developing microfluidic vascular or cell culture models may include ECM hydrogel patterning, which may be achieved using micropillars, microneedle/glass capillaries, ECM scaffolds, viscous finger printing or sacrificial gelation.

ECM loading using micropillars or microposts have been reported a few years ago. Briefly, micropillar array (about 50 μm to 200 μm spacing) is placed between channels, and 3D ECM hydrogel loading occurs between pillars, which prevent gel leakage into adjacent channels. This allows spatial patterning of multiple cell types in different channels and may be used to study angiogenesis or tumor cells intravasation through endothelium. However, a significant limitation of this technique lies in the geometrical constraint as vascular channel designs are typically configured to be straight so as to avoid gel leakage. It is thus difficult to create pathological vessel geometries such as bifurcation, stenosis or aneurysm using this method. In addition, the ECM/vascular cells interface is non-continuous due to presence of the pillar array. This adversely affects perfusion-based studies as vascular cells experience different biomechanical cues depending on their positions on either ECM (soft) or PDMS micropillar (hard) support.

Regarding microneedle/glass capillaries technique, the micron-sized needles are inserted into the ECM hydrogel during gel polymerization and subsequently removed to create circular lumens. Co-culture systems may be set up to mimic physiological microenvironment by seeding vascular cells in the circular channels while pericytes are typically embedded within the surrounding ECM. For greater spatial control on the cell organisation, a combination of different sized needles to create multiple vessel walls may be used. Vascular cells, smooth muscle cells and fibroblasts are seeded layer by layer as each needle is removed from the ECM. Yet, the fabrication process for such techniques tends to be complicated and the resultant vascular channel is straight due to shape of the needle. While this issue may be overcome by using poly(methyl methacrylate) (PMMA) optical fibre, which allows easy shape modification to create various vascular geometries, such a technique has been specifically demonstrated with PDMS and not for softer materials, such as hydrogel, due to fabrication difficulties with softer materials.

Meanwhile, in ECM scaffolding, microfluidic microvessel network may be created in collagen scaffold using complicated multi-step lithography, and chip assembly remains technically challenging. Microvascular bed may be created by vasculogenesis through co-culture of endothelial cells, stromal cells and fibrin for about 2 to 3 weeks in 3D collagen. This is time consuming and new vessel formation is often random with uncontrolled spatial orientation.

As for viscous finger printing, it is a technique developed to generate lumens through ECM hydrogels in microfluidic systems. Briefly, manual pipetting of liquid media (less vicious) into unpolymerized hydrogel creates a lumen, which may be later polymerized to form perfusable microchannels for vascular cells. However, the cross-sectional shape of the lumen remains irregular and difficult to control, and the method is more robust for straight channel designs and not for pathologically complex geometries.

In sacrificial gelation, microfluidic structures made of gelatin serve as a sacrificial template for collagen patterning, which is subsequently melted to form perfusable microchannels embedded in collagen. This enables channel fabrication of different geometries, but the technique requires polymerization of two different hydrogels with compatible gelation properties.

Holistically, the aforementioned techniques tend to be time consuming with complicated fabrication process, do not allow creation of complex pathological vascular geometries and lack flexibility for forming continuous ECM/vascular cells interface.

There is thus a need to provide for an improved method for patterning microchannel of different vascular geometries in ECM hydrogel efficiently while addressing the above limitations. The improved method should also allow for hydrogel loading to be performed by manual pipetting, which may be operated by non-skilled personnels without requiring any specialized equipment.

There is also a need to provide for a device that enables such a method to resolve and/or ameliorate the issues mentioned above.

SUMMARY

In one aspect, there is provided for a device for patterning extracellular matrix hydrogel comprising: a first layer comprising a surface patterned to define a microchannel; a second layer comprising a loading channel in fluid communication with one or more loading ports for receiving the extracellular matrix hydrogel, wherein the first layer is attached over the second layer with the patterned surface facing the loading channel to define an open chamber with one or more regions having a cross-sectional area reduced by the patterned surface, and wherein the extracellular matrix hydrogel is confined to fill the one or more regions having the reduced cross-sectional area, thereby forming a perfusable channel in the open chamber.

In another aspect, there is provided for a device for patterning extracellular matrix hydrogel comprising: a first layer comprising a surface patterned to define at least one microchannel; a substrate for receiving the extracellular matrix hydrogel, wherein the substrate comprises no loading channel, wherein the first layer is attached over the substrate with the patterned surface facing the substrate to define an open chamber with one or more regions having a cross-sectional area reduced by the patterned surface, and wherein the extracellular matrix hydrogel is confined to fill the one or more regions having the reduced cross-sectional area, thereby forming at least one perfusable channel in the open chamber.

In another aspect, there is provided for a method of patterning extracellular matrix hydrogel, comprising: providing a device as disclosed above; loading the extracellular matrix hydrogel into the device; and polymerizing the extracellular matrix hydrogel in one or more regions of the device having a reduced cross-sectional area to form at least one perfusable channel in an open chamber of the device.

BRIEF DESCRIPTION OF THE DRAWINGS

In the drawings, like reference characters generally refer to like parts. As an example, a part labelled with reference numeral 100 in one of the figures refers to the same part labelled with reference numeral 100' in another figure.

The drawings are not necessarily to scale, emphasis instead generally being placed upon illustrating the principles of the invention. In the following description, various embodiments of the present disclosure are described with reference to the following drawings, in which:

FIG. 1a shows the top and bottom templates/layers of a multilayer polydimethylsiloxane (PDMS) device for extracellular matrix (ECM) hydrogel patterning fabricated according to embodiments disclosed herein. Specifically, the left image shows various ECM loading channel configurations having multiple gel loading ports (bottom template/layer) while the right image shows vascular microchannel designs (top template/layer). The latter helps to define the boundaries of where the ECM hydrogel may be confined to.

FIG. 2a shows three brightfield images of the functional microdevice for ECM hydrogel loading. Specifically, the left image of FIG. 2a shows an ECM loading channel (bottom layer) aligned with a microchannel (top layer) having a T-junction geometry. Type I collagen (2.5 mg/ml) added with food dye was used to exemplify the hydrogel patterned perfusable channel as shown in center and right images of FIG. 2a.

FIG. 2b shows three brightfield images of the functional microdevice for ECM hydrogel loading. Specifically, the left image of FIG. 2b shows an ECM loading channel (bottom layer) aligned with a microchannel (top layer) having a serpentine geometry. Type I collagen (2.5 mg/ml) added with food dye was used to exemplify the hydrogel patterned perfusable channel as shown in center and right images of FIG. 2b.

FIG. 2c shows three brightfield images of the functional microdevice for ECM hydrogel loading. Specifically, the left image of FIG. 2c shows an ECM loading channel (bottom layer) aligned with a microchannel (top layer) having a Y-junction geometry. Type I collagen (2.5 mg/ml) added with food dye was used to exemplify the hydrogel patterned perfusable channel as shown in center and right images of FIG. 2c.

FIG. 2d shows three brightfield images of the functional microdevice for ECM hydrogel loading. Specifically, the left image of FIG. 2d shows an ECM loading channel (bottom layer) aligned with a microchannel (top layer) having a filleted Y-junction geometry. Type I collagen (2.5 mg/ml) added with food dye was used to exemplify the hydrogel patterned perfusable channel as shown in center and right images of FIG. 2d.

FIG. 4b shows a fluorescence intensity linescan within the ECM hydrogel region at different timepoints (0 min, 60 mins, 120 mins and 180 mins)

indicating long term and stable diffusion gradient. The perfusable channel loaded with FITC-dextran (40 kDa) has a width of 600 µm.

Figure 5:
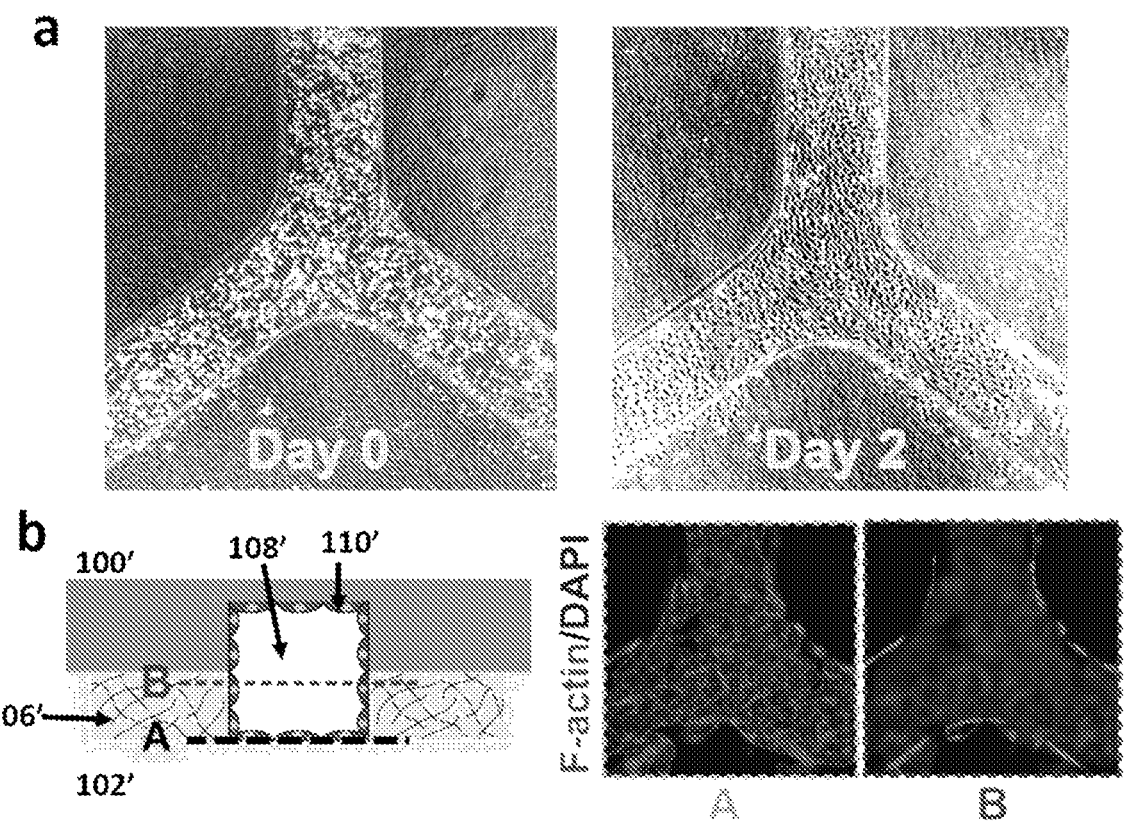

FIG. 5a shows HUVECs in the collagen-patterned microdevice. Specifically the left image of FIG. 5a is a phase contrast image showing HUVECs seeding at day 0 and the right image of FIG. 5a is a phase contrast image showing formation of the confluent cell monolayer at day 2.

FIG. 5b shows HUVECs in the collagen-patterned microdevice. Specifically the left image of FIG. 5b shows the z-positions (A and B) in the perfusable channel at which fluorescence images of the cell monolayer in the fabricated microfluidic device (the two right images of FIG. 5b) were taken. In the first right image of FIG. 5b (represented by image A), the cells were confluent at the bottom of the perfusable channel (corresponding to position A in left image of FIG. 5b). In the second right image of FIG. 5b (represented by image B), a monolayer was observed along the collagen walls (corresponding to position B in the left image of FIG. 5b).

Figure 6:
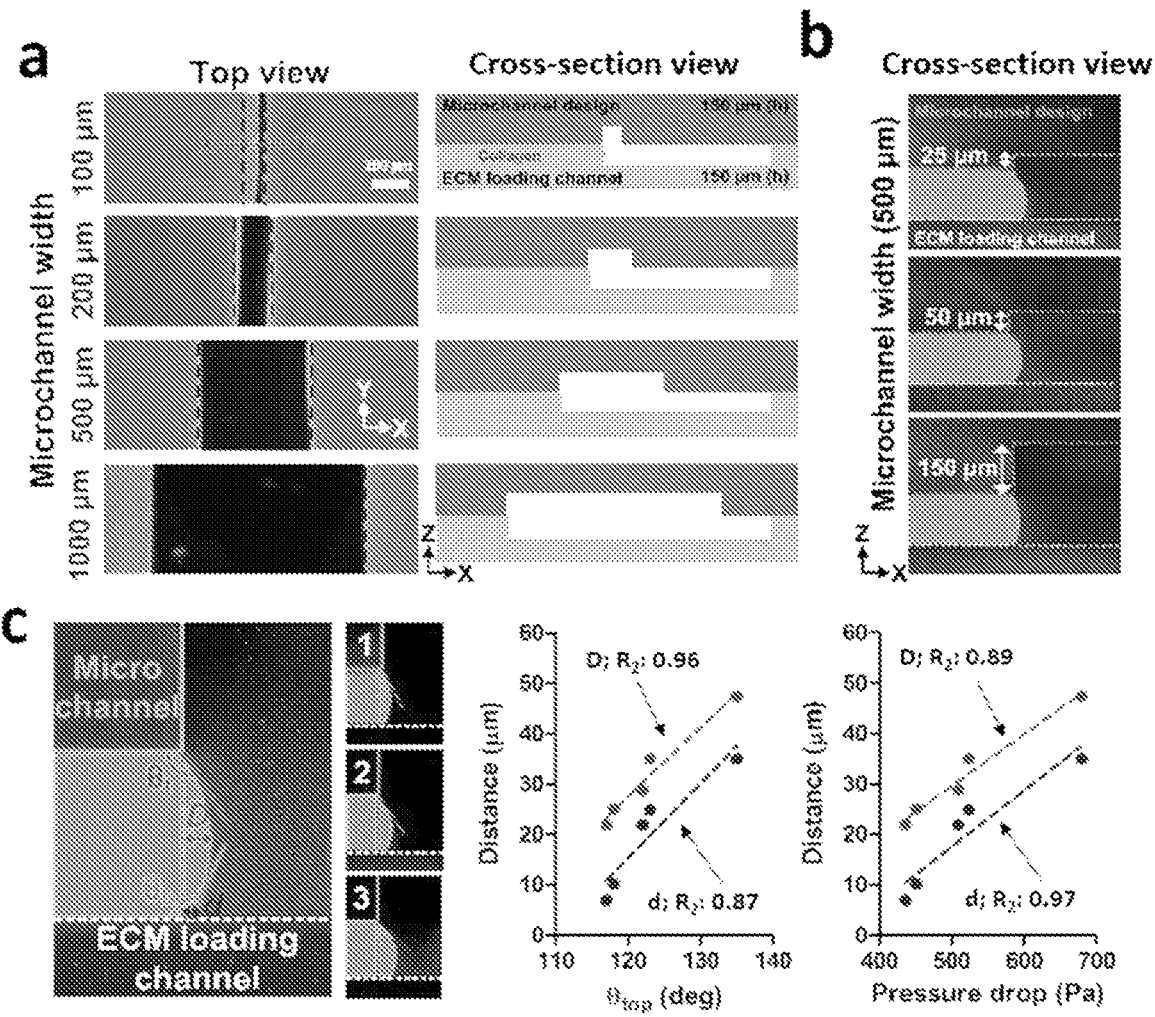

FIG. 6a shows fluorescence images of perfusable channels patterned using FITC laden collagen gel (left images; scale bar represents 200 µm). The corresponding cross-section schematics indicating the corresponding channel dimensions of 100 µm, 200 µm, 500 µm and 1000 µm are shown in right image of FIG. 6a.

FIG. 6b shows the cross-sectional view of FITC-laden collagen gel based on different microchannel depths.

FIG. 6c shows fluorescence images of FITC-laden collagen gel inside sectioned chips (sectioned along x-x' as shown in top left image of FIG. 6a) illustrating increase in top contact angle ($\theta_t$) while collagen remained pinned at the top edge with higher loading pressure. Insets 1, 2 and 3 highlight the pinning effect of the collagen at the top edge with increasing loading pressure. The plot in the center of FIG. 6c indicates strong linearity between $\theta_t$ ($\theta_{top}$) and the maximum gel distance (D; which is measured at centre of the collagen bulge), and the gel distance along the bottom surface (d). The plot in the right of FIG. 6c indicates strong linearity between the pressure drop and maximum gel distance (D; which is measured at the centre of the collagen bulge), and the gel distance along the bottom surface (d).

Figure 7:
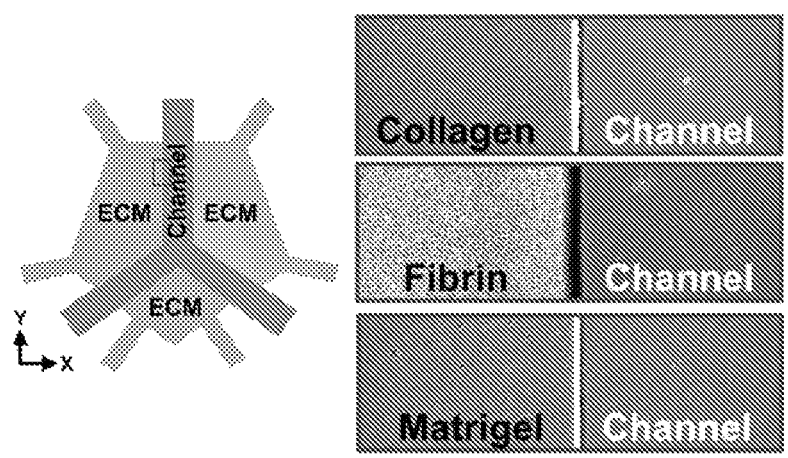

FIG. 7 illustrates patterning of different ECM hydrogels. Specifically, the left image of FIG. 7 is a schematic of a Y-channel microfluidic device while the right image of FIG. 7 shows magnified brightfield images of ECM hydrogel patterns using collagen, fibrin and Matrigel.

Figure 8:
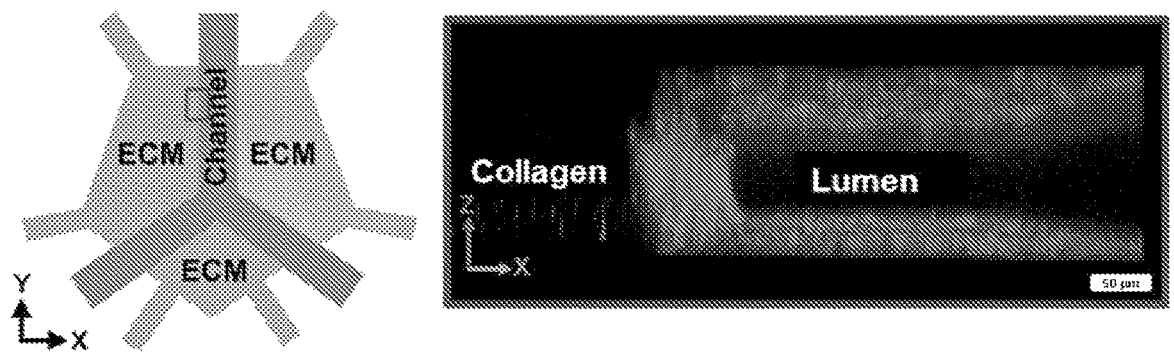

FIG. 8 shows HUVECs in the collagen-patterned microdevice. Specifically, the left image of FIG. 8 is a schematic of a Y-channel microfluidic device while the right image of FIG. 8 shows a confocal image of a section of the microvasculature highlighting the HUVECs monolayer along the ECM hydrogel sidewall. Scale bar represents 50 µm.

Figure 9:
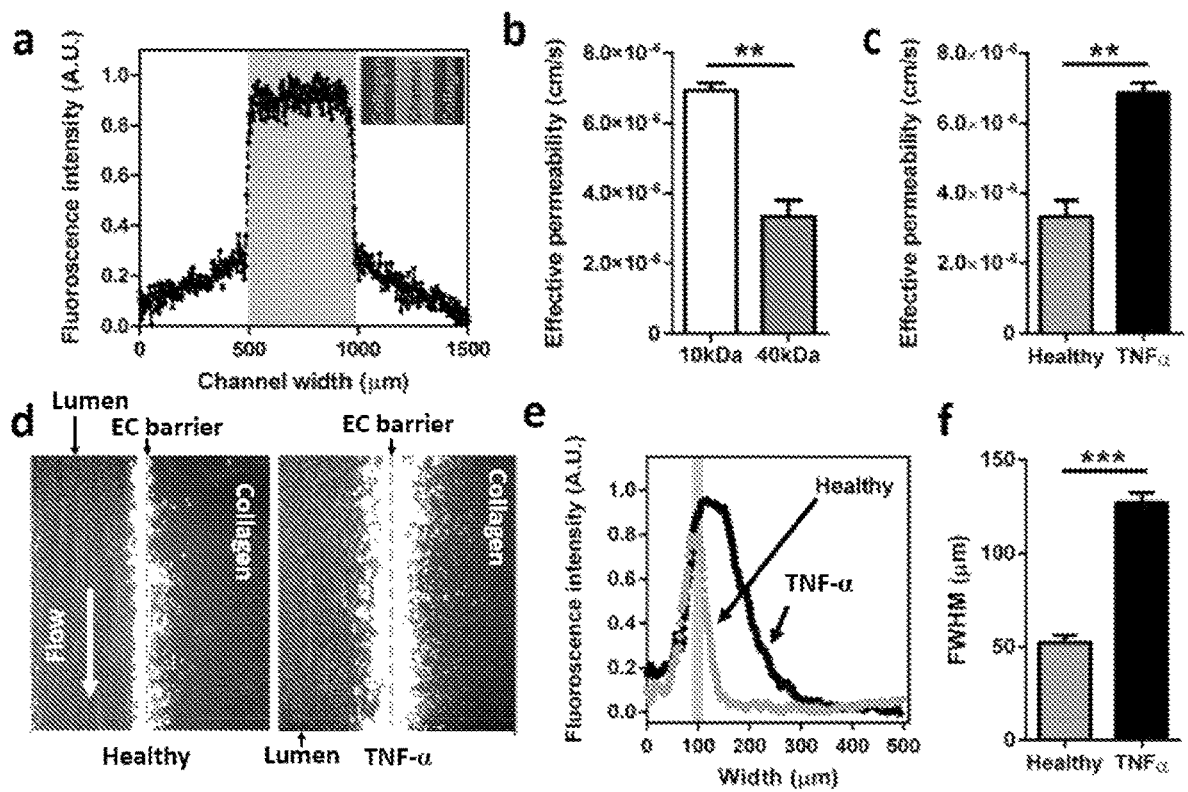

FIG. 9a shows the characterization of endothelial HUVECs barrier function. Specifically, FIG. 9a shows the fluorescence intensity linescan and image of the perfusable channel loaded with FITC-conjugated Dextran (40 kDa). The higlighted region indicates the perfusable channel position.

FIG. 9b shows the characterization of endothelial HUVECs barrier function. Specifically, FIG. 9b shows the selective barrier permeability of the endothelial monolayer using FITC-conjugated dextran molecules of different molecular weights (10 kDa and 40 kDa) (n=4). Data are presented as mean±s.d. (s.d. refers to standard deviation,  refers to $p<0.01$, * refers to $p<0.001$).

FIG. 9c shows the characterization of endothelial HUVECs barrier function. Specifically, FIG. 9c shows significant increase in endothelial barrier permeability when treated with TNF-α (n=4; TNF-α represents tumor necrosis factor alpha). Data are presented as mean±s.d. ( refers to $p<0.01$, * refers to $p<0.001$).

FIG. 9d shows the characterization of endothelial HUVECs barrier function. Specifically, FIG. 9d shows representative images illustrating convective barrier permeability under flow. 2 µm beads penetrated further into the collagen gel for TNF-α treated endothelial cells (EC) (right image of FIG. 9d) as compared to healthy EC (left image of FIG. 9d).

FIG. 9e shows the characterization of endothelial HUVECs barrier function. Specifically, FIG. 9e shows a plot indicating penetration of 2 µm beads into collagen gel. Shaded line (at 100 µm) corresponds to position of EC barrier. Data are presented as mean±s.d. ( refers to $p<0.01$, * refers to $p<0.001$).

FIG. 9f shows the characterization of endothelial HUVECs barrier function. Specifically, FIG. 9f characterizes full width at half maximum (FWHM) of the fluorescent spectrum for healthy and TNF-α treated EC (n=4). Data are presented as mean±s.d. ( refers to $p<0.01$, * refers to $p<0.001$).

Figure 10:
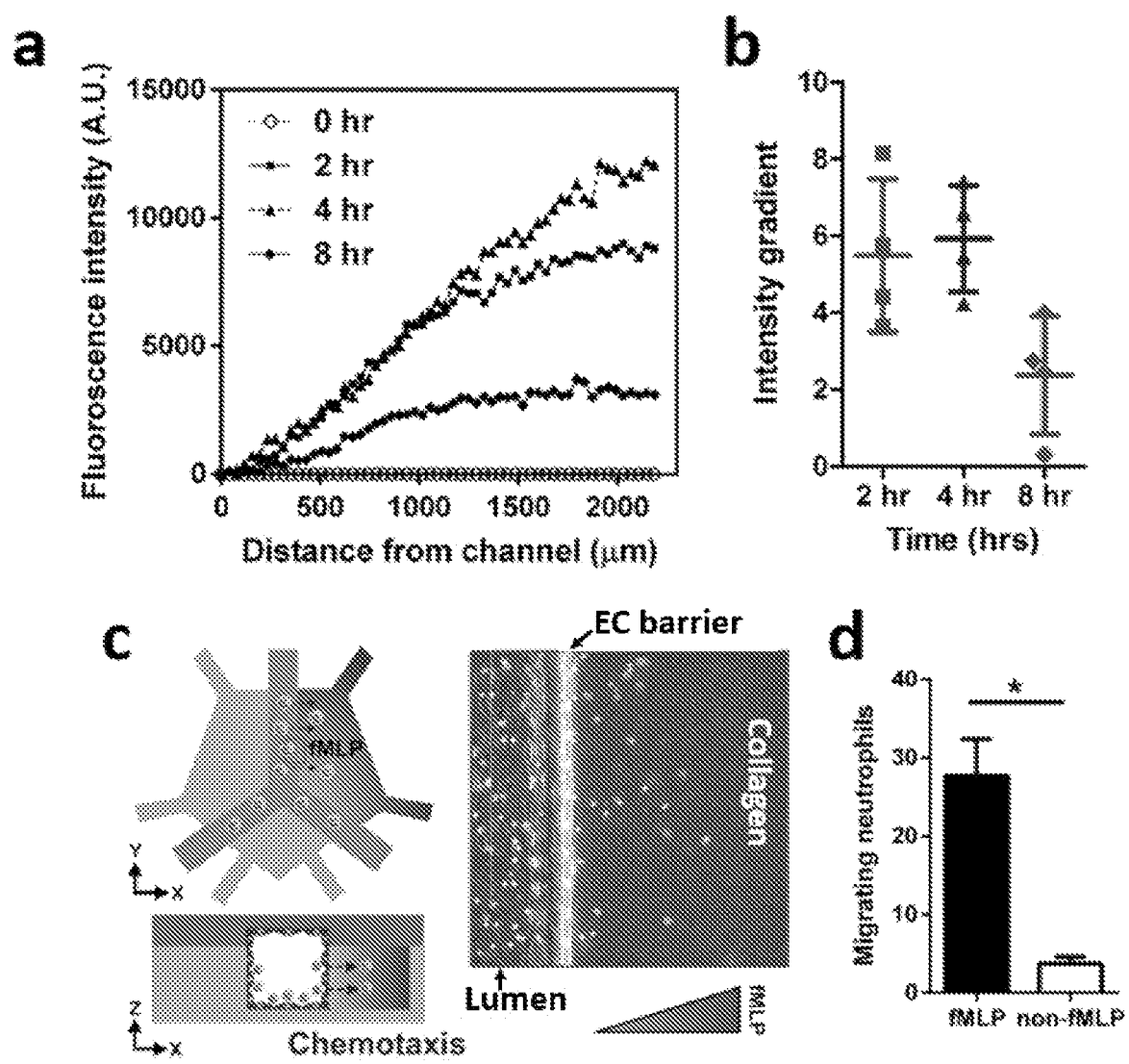

FIG. 10a indicates the results of neutrophil chemotaxis in a stable chemoattractant (fMLP: N-formylmethionine-leucyl-phenylalanine) concentration gradient. Specifically, FIG. 10a shows a plot illustrating the fluorescent linescan of FITC dye (fMLP) in the collagen gel over different time points. All values are normalized to time T=0 hour.

FIG. 10b indicates the results of neutrophil chemotaxis in a stable chemoattractant concentration gradient. Specifically, FIG. 10b shows a plot highlighting gradient of the various curves of FIG. 10b, which further suggests the creation of a stable gradient.

FIG. 10c indicates the results of neutrophil chemotaxis in a stable chemoattractant concentration gradient. Specifically, FIG. 10c shows that the chemoattractant fMLP is introduced at one side of the collagen gel to create a concentration gradient for neutrophil migration. Brightfield image shown in right of FIG. 10c illustrates neutrophil migration across the HUVECs barrier into the collagen gel after 2 hours.

FIG. 10d indicates the results of neutrophil chemotaxis in a stable chemoattractant concentration gradient. Specifically, FIG. 10d indicates the cell count of the migrated neutrophils in the presence and absence of fMLP (n=4). Data are presented as mean±s.d. (* refers to $p<0.05$).

Figure 11:
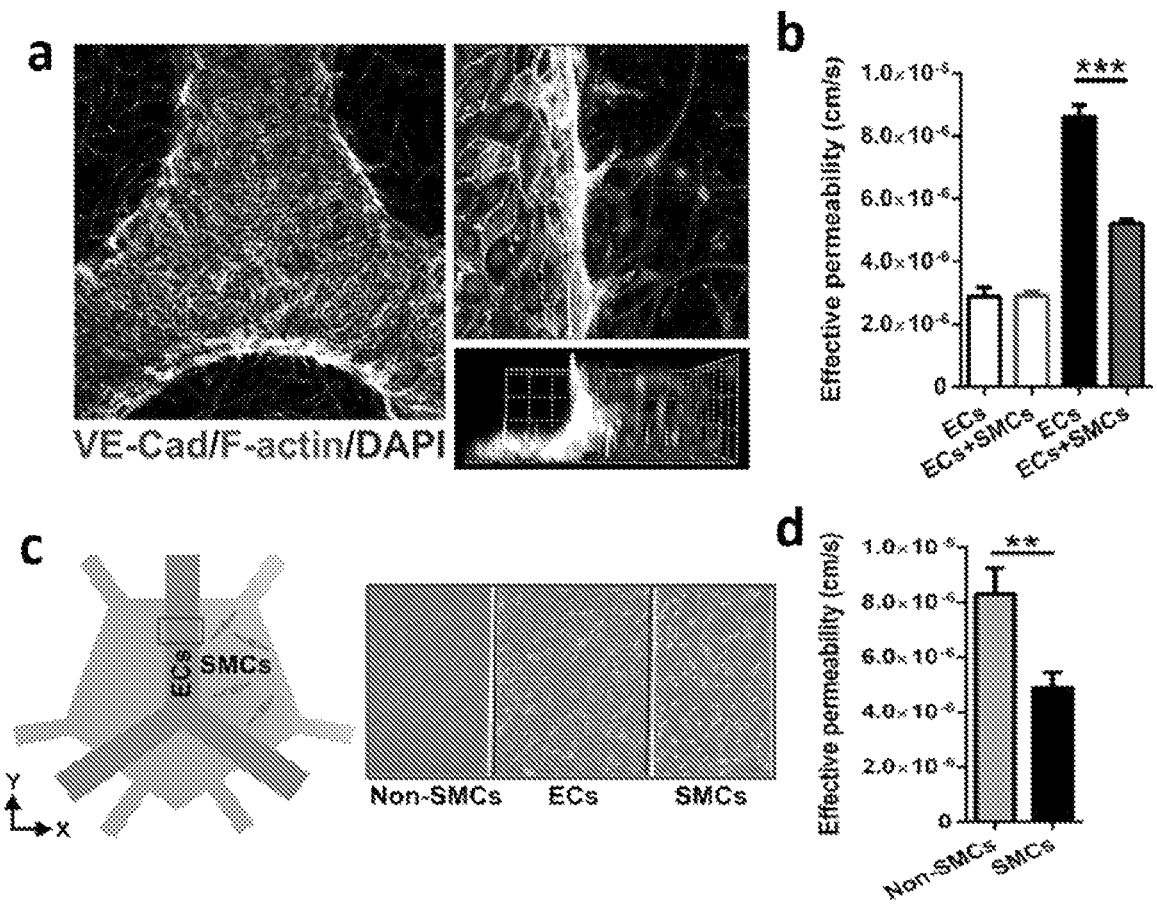

FIG. 11a illustrates the results for endothelial-smooth muscle cells (EC-SMC) co-culture system. Specifically, FIG. 11a shows confocal images of the endothelialized perfusable channel surrounded by aortic smooth muscle cells (SMCs). The upper right image in FIG. 11a is an inset showing a magnified section of the EC-SMC boundary and the bottom right image in FIG. 11a shows its corresponding Z-stacked image to illustrate 3D arrangement of different cell types.

FIG. 11b illustrates the results for EC-SMC co-culture system. Specifically, FIG. 11b shows a comparison of EC barrier permeability with and without SMC in healthy (unshaded) and TNF-α treated (solid-shaded) conditions. Data are presented as mean±s.d. (* refers to $p<0.05$,  refers to $p<0.01$, * refers to $p<0.001$).

FIG. 11c illustrates the results for EC-SMC co-culture system. Specifically, FIG. 11c shows SMC introduced into one side of the collagen gel while the other sides are kept without SMCs. The insets in the right of FIG. 11c show the brightfield images of a section of the chip with SMC on one side of the HUVECs channel.

FIG. 11d illustrates the results for EC-SMC co-culture system. Specifically, FIG. 11d shows the barrier permeability of inflamed endothelium measured from either side of the HUVEC channel. SMCs reduced the leakiness of the endothelial barrier (n=4). Data are presented as mean±s.d. (* refers to p<0.05,  refers to p<0.01, * refers to p<0.001).

Figure 12:
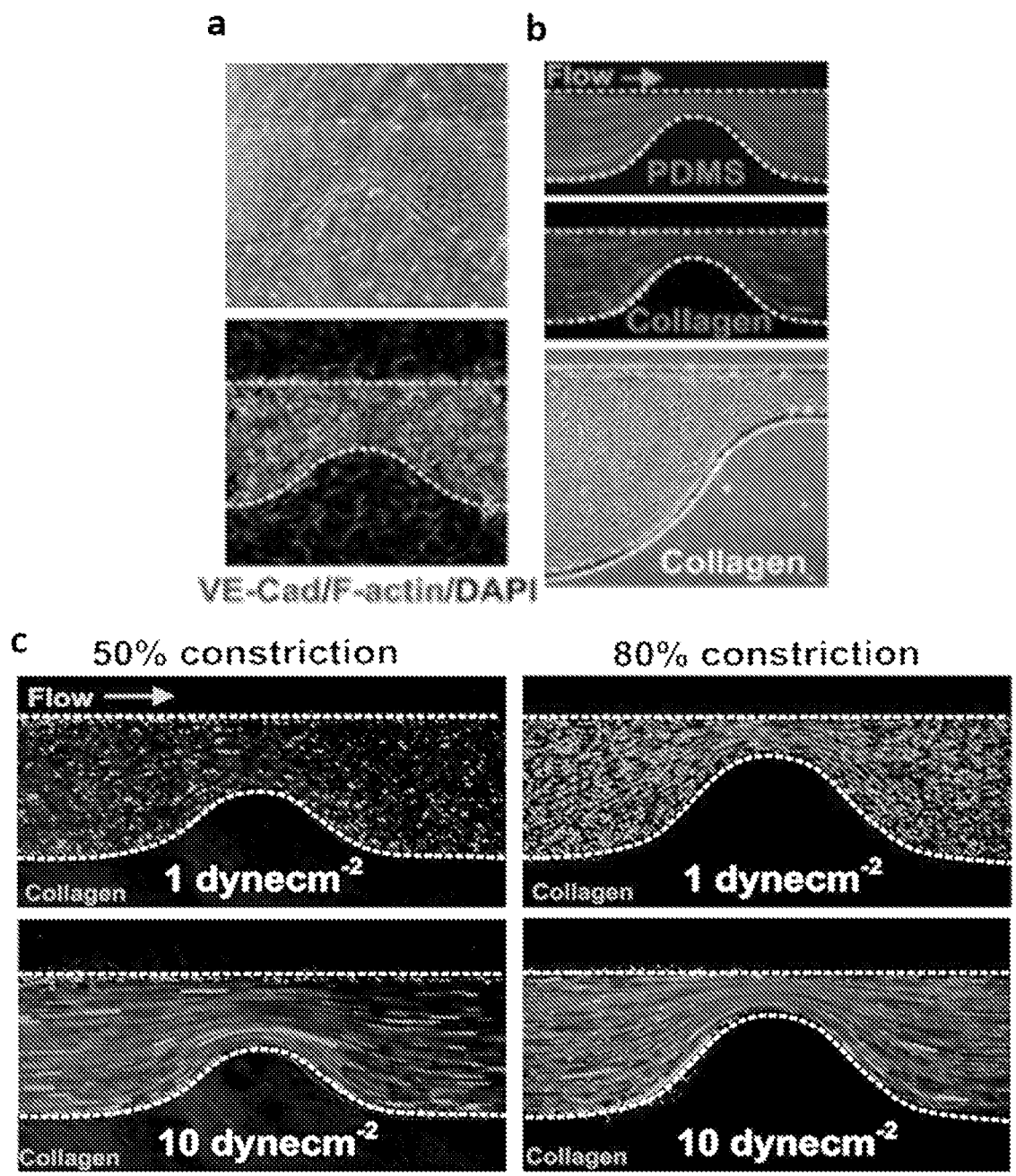

FIG. 12a illustrates a vascular stenosis model developed based on the present method and device. Specifically, FIG. 12a shows a bright field image (top) and a confocal (bottom) image of an endothelialized lumen surrounded by SMC in a perfusable channel with 50% collagen-patterned constriction.

FIG. 12b illustrates a vascular stenosis model developed based on the present method and device. Specifically, the two images at top of FIG. 12b are representative fluorescent images illustrating perfusion of FITC-conjugated 2 μm beads in a perfusable channel with PDMS and collagen-patterned constriction (80%). It is observable that the beads accumulated at the proximal edge (represented by arrows) of the collagen bump at an inlet wall shear stress of 10 dyne $cm^{-2}$ (1 Pa). Meanwhile, the bottom of FIG. 12b is a composite image indicating beads accumulation at the EC barrier in an endothelialised perfusable channel.

FIG. 12c illustrates a vascular stenosis model developed based on the present method and device. Specifically, FIG. 12c shows fluorescent images of FITC-conjugated 2 μm beads at different flow rates in perfusable channels with different channel constrictions. No beads accumulation was observed for 50% constriction at 10 dyne $cm^{-2}$ (1 Pa) while beads accumulated (see arrows) for 80% constriction.

Figure 13:
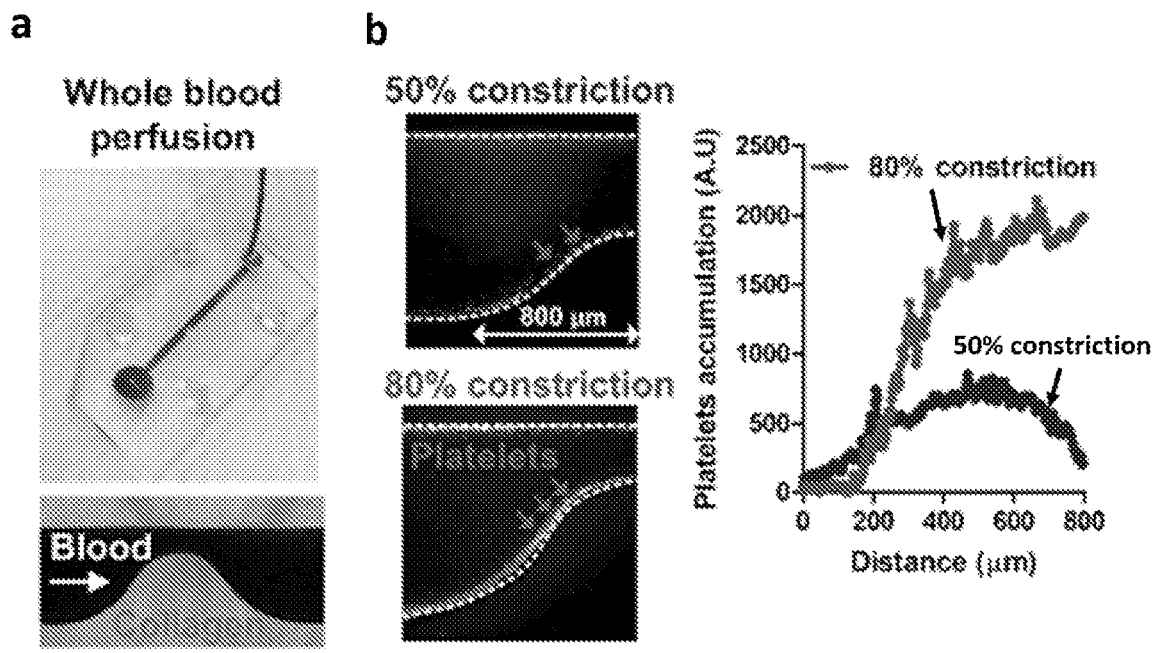

FIG. 13a shows the results of whole blood perfusion through the stenosis chip. Specifically, FIG. 13a illustrates whole blood perfusion through a microfluidic chip with collagen-patterned constriction (80%).

FIG. 13b shows the results of whole blood perfusion through the stenosis chip. Specifically, FIG. 13b characterizes platelet (R6G-stained) binding at the proximal region of the 50% and 80% collagen constriction under whole blood perfusion at 10 dyne $cm^{-2}$ (1 Pa). The representative images (two left images) and fluorescent intensity plot (right image) indicate significant platelet accumulation (see arrows) in the 80% constricted perfusable channel.

Figure 14:
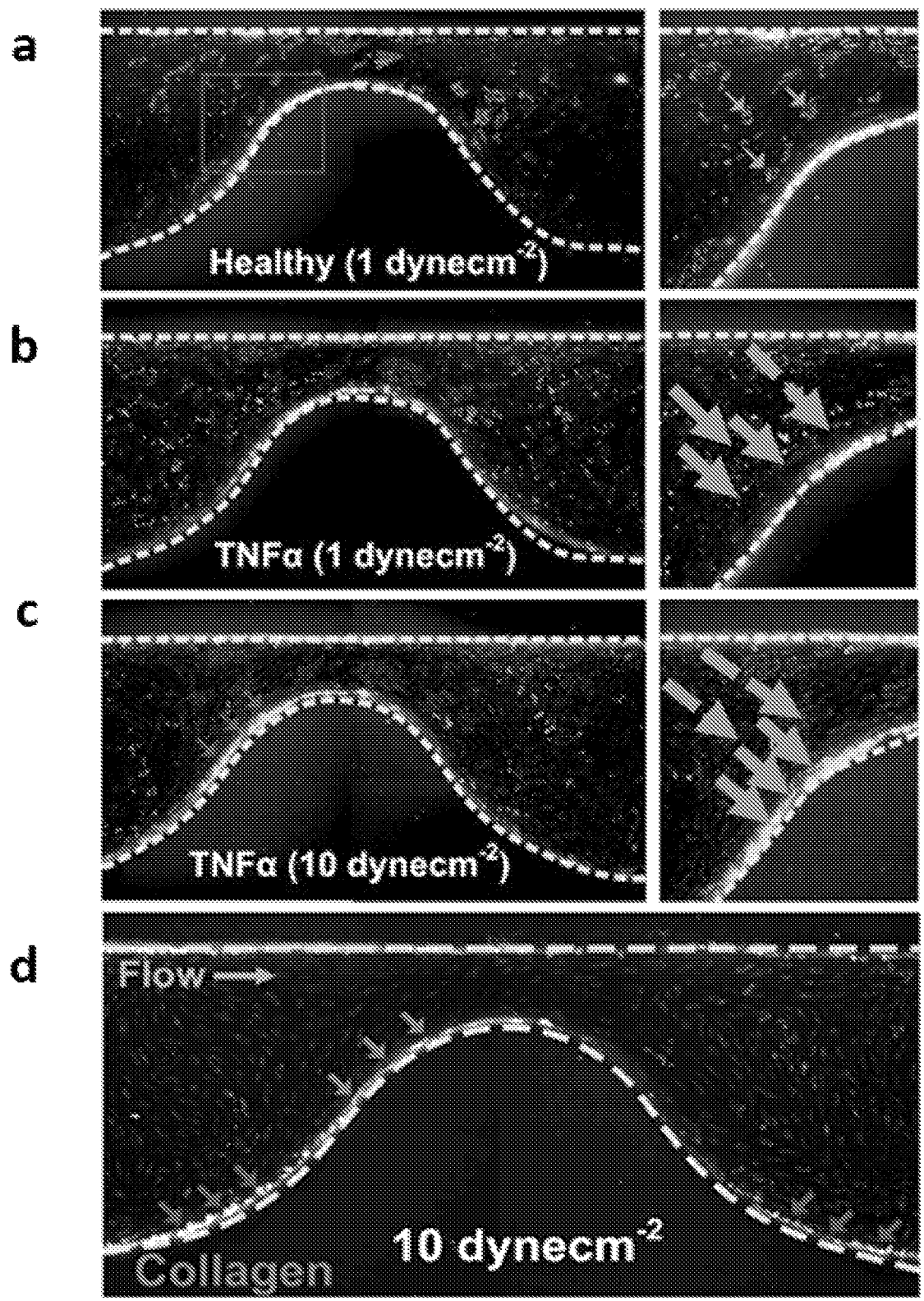

FIG. 14a illustrates endothelial-blood cell interactions during vascular inflammation. Specifically, FIG. 14a is a representative fluorescence image of healthy endothelium after 15 mins of whole blood (R6G-stained) perfusion at 1 dyne $cm^{-2}$ (0.1 Pa). Magnified image of the proximal region (as highlighted by the box and shown in the right inset image of FIG. 14a) focusing on the constriction, highlights platelet adhesion (as shown by the arrows).

FIG. 14b illustrates endothelial-blood cell interactions during vascular inflammation. Specifically, FIG. 14b is a representative fluorescence image of the inflamed endothelium (TNF-α treated) after 15 mins of whole blood perfusion at 1 dyne $cm^{-2}$ (0.1 Pa). Magnified image indicating platelets (represented by the single broken arrow) and leukocytes (represented by the solid arrows) adhesion are shown in the right inset of FIG. 14b.

FIG. 14c illustrates endothelial-blood cell interactions during vascular inflammation. Specifically, FIG. 14c is a representative fluorescence image of the inflamed endothelium (TNF-α treated) after 15 mins of whole blood perfusion at 10 dyne $cm^{-2}$ (0.1 Pa). In the right inset image (magnified) of FIG. 14c, the two broken and three solid arrows indicate significant accumulation of platelets and leukocytes-platelets at the proximal edge of the occlusion, respectively.

FIG. 14d illustrates endothelial-blood cell interactions during vascular inflammation. Specifically, FIG. 14d is a fluorescence image of the entire stenosis region highlighting platelets and leukocytes adherence at both proximal and distal regions (the six bottom arrows) of the collagen-patterned constriction (80%) and increased platelet binding (the three arrows towards the top) at the proximal region nearer the channel constriction with additional convective flow into the ECM (collagen).

Figure 15A:
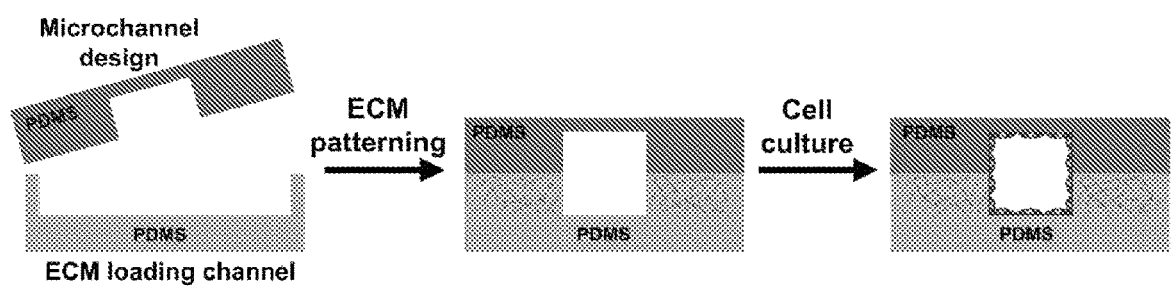

FIG. 15a is a schematic diagram showing the present method which utilizes two layers of PDMS.

Figure 15B:
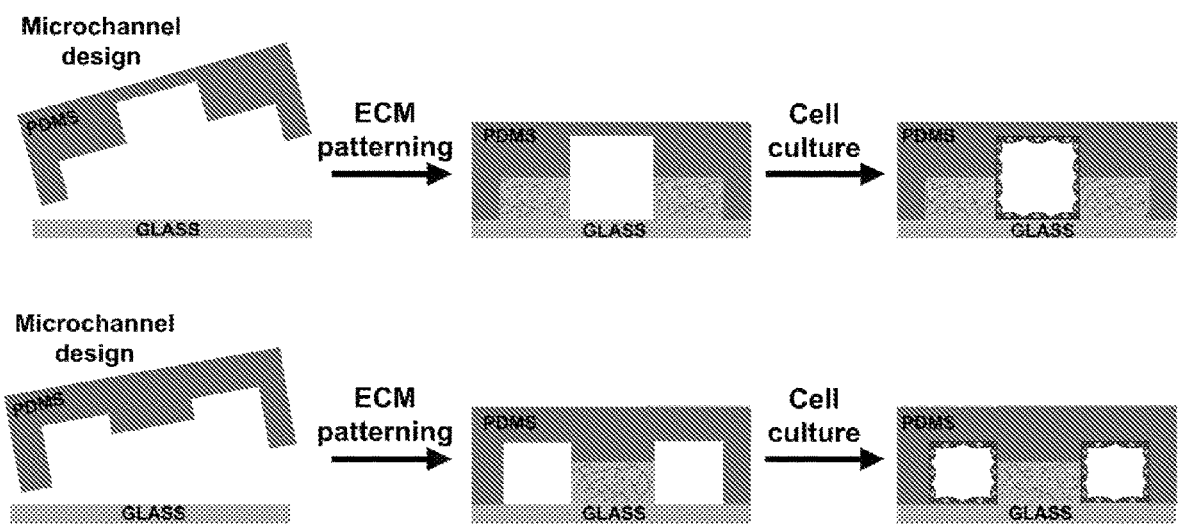

FIG. 15b is a schematic diagram showing modifications of the present method depicted in FIG. 15a. Instead of using two PDMS layers, a single layer of PDMS (patterned with structures having same or different depths/heights) bonded to a substrate (e.g. glass slide) is utilized in the modified method.

Figure 16:
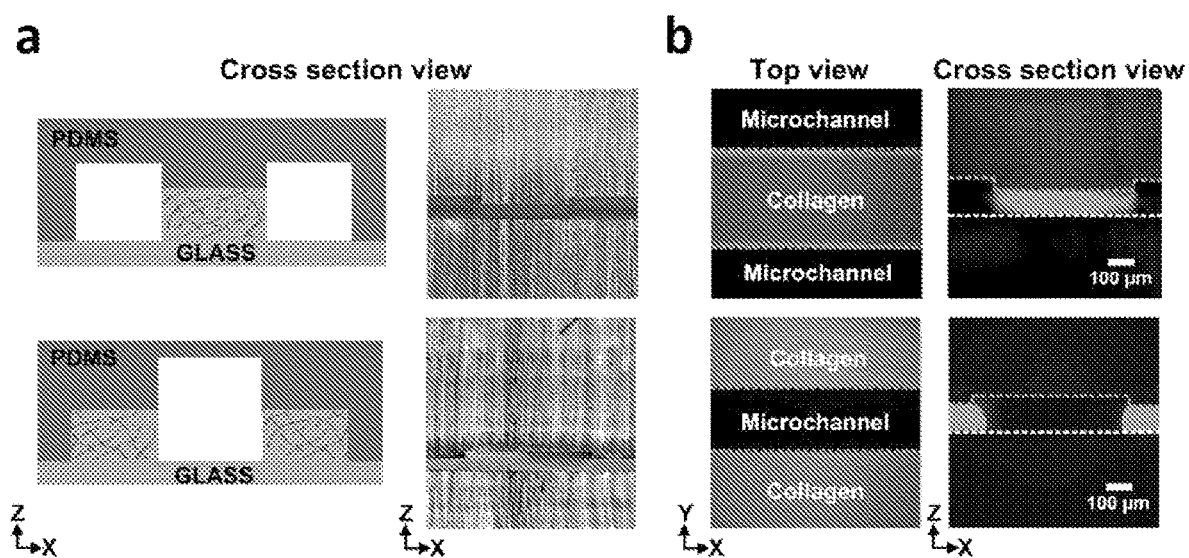

FIG. 16a shows a schematic (left images) and its corresponding cross-sectional view (right images) of the different chip configurations derived from a two-step photolithography procedure.

FIG. 16b shows characterization results of the two-step photolithography procedure. Specifically, FIG. 16b shows microscopic images of the top view and the cross-sectional view of the chip with FITC-laden hydrogel. The creation of differential heights/depths inside the open chamber holds the ECM hydrogel in their respective regions (where the cross-section area is reduced) due to the capillary burst valves (CBV) effect.

DETAILED DESCRIPTION

The following detailed description refers to the accompanying drawings that show, by way of illustration, specific details and embodiments in which the invention may be practised.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

The present disclosure describes a method for rapid 3D patterning of extracellular matrix (ECM) hydrogel for in vitro microfluidic vascular models. This strategy advantageously enables fabrication of perfusable ECM hydrogel patterned vascular architectures and living cells, even including those with complicated pathological geometries which conventional methods fail to produce or have difficulties producing.

Advantageously, the present device and method enable rapid patterning of ECM hydrogel for in vitro microfluidic vascular models. The technique requires two polydimethylsiloxane (PDMS) layers, one patterned with loading channel(s) for ECM hydrogel loading (bottom), and the other patterned with vascular microchannel(s) design (top) as template. The technique may also utilize only one PDMS layer patterned with designs of both the vascular microchannel and the loading channel, and another flat substrate. The ECM hydrogel patterning may then be achieved by surface tension, at boundaries defined by the vascular channel(s), to form perfusable channel(s) of different geometries without involving complicated techniques. Accordingly, microfluidic vascular models that mimic real life vascular models may be easily created.

The present device and method are also advantageous in that they mitigate or even entirely circumvent the limitations posed by conventional methods. For instance, conventional microfluidic methods, such as micropillars, may lead to generation of bubbles between the micropillars which hinder study of barrier functions and cell-cell interactions during perfusion. The present device and method, which do not require such micropillars, circumvent such an issue.

Accordingly, the present device and method are further advantageous in that they can be used to develop various types of microfluidic models to aid in various kinds of research and not just for studying one specific vascular models.

Having outlined various advantages of the present device and method, definitions of certain terms are first discussed before going into details of the various embodiments.

The word "over" used in the context of arranging, forming, or even attaching a top layer to a bottom layer, means that the top layer may be formed "directly on", e.g. in direct contact with, the implied side or surface of the bottom layer. In other words, a first layer "over" a second layer may refer to the first layer directly on the second layer without any intervening elements between the first and second layers.

In the context of the present disclosure, the phrase "perfusable" when used with reference to a channel, refers to a channel that allows biological substance(s) to proliferate, flow or spread in. For example, a channel that is supplied with a cell culture may allow the cells to flow or proliferate in the channel.

The word "substantially" does not exclude "completely" e.g. a composition which is "substantially free" from Y may be completely free from Y. Where necessary, the word "substantially" may be omitted from the definition of the invention.

In the context of various embodiments, the articles "a", "an" and "the" as used with regard to a feature or element include a reference to one or more of the features or elements.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A and B" may include A or B or both A and B. Correspondingly, the phrase of the form of "at least one of A and B and C", or including further listed items, may include any and all combinations of one or more of the associated listed items.

Unless specified otherwise, the terms "comprising" and "comprise", and grammatical variants thereof, are intended to represent "open" or "inclusive" language such that they include recited elements but also permit inclusion of additional, unrecited elements.

Having defined the various terms as mentioned above, details of the various embodiments are now described below.

In the present disclosure, there is provided for a device for patterning extracellular matrix hydrogel comprising: a first layer comprising a surface patterned to define a microchannel; a second layer comprising a loading channel in fluid communication with one or more loading ports for receiving the extracellular matrix hydrogel, wherein the first layer is attached over the second layer with the patterned surface facing the loading channel to define an open chamber with one or more regions having a cross-sectional area reduced by the patterned surface, and wherein the extracellular matrix hydrogel may be confined to fill the one or more regions having the reduced cross-sectional area, thereby forming a perfusable channel in the open chamber.

In various embodiments of the present device, the first layer refers to the layer having a surface patterned to define a microchannel. The surface of this first layer may be patterned using any known methods to form the microchannel, such as photolithography and/or soft lithography. In other words, the first layer of the present device may refer to a layer that is pre-formed with a microchannel. The term "microchannel" is thus specifically used with reference to the first layer.

The microchannel, together with the second layer, may be used to impart a geometrical configuration onto the present device. That is to say, the first layer containing the microchannel serves as one of the components for forming a device for ECM hydrogel patterning, particularly imparting a desired vascular microchannel design onto the present device.

The geometrical configuration of the microchannel may be of any random geometry, whether simple or complex, such as a linear microchannel, a curved microchannel etc. The microchannel may comprise a T-shaped junction, a serpentine junction, a Y-shaped junction or a filleted Y-shaped junction. Advantageously, as the microchannel can take on various geometrical configurations, it is able to impart even the most complex geometrical design onto the device, such as vascular structures or pathological networks.

Since the surface(s) of the first layer needs to be patterned, a suitable material that is not too soft, till the point that it becomes too difficult to retain any imprinted configuration, may be used. Hence, the first layer may be an imprintable material. Such imprintable material may include, but not limited to, polydimethylsiloxane (PDMS), poly(methyl methacrylate) (PMMA), polycarbonate, glass, cyclic olefin copolymer, polystyrene or silicon. The first layer may thus comprise or consist of polydimethylsiloxane (PDMS). The second layer may also be made from the same or different imprintable material. In some embodiments, both the first layer and the second layer may comprise PDMS.

In various embodiments of the present device, there is also the second layer, which may be combined with the first layer to form the device for patterning ECM hydrogel. The second layer may comprise a loading channel in which the ECM hydrogel is supplied to. The second layer (its surface(s)) may be patterned to form the loading channel. The pattern form on a surface of the second layer (defining the loading channel) may be squared, rectangular, circular, pentagonal etc. That is to say, the loading channel may be of any configuration. It is to be distinguished that these shapes or configurations refer to the pattern on the surface of the second layer (i.e. the loading channel) and not the cross-section of the loading channel. The phrase "loading channel" or "ECM loading channel" may be used with reference to the second layer in the context of embodiments that have such a second layer.

The techniques used to pattern surface of the second layer may be the same technique(s) for patterning first layer as mentioned above. As shape of the loading channel and design of the microchannel may be customised, this makes the present device, and thus the method, advantageously versatile for creating any designs in microfluidic models.

The second layer may be an imprintable material, such as PDMS. The second layer may be of the same or different material from the first layer as mentioned above.

The ECM hydrogel to be supplied to the loading channel may be loaded or injected into loading ports found in the second layer. These loading ports may be in fluid communication with the loading channel, such that the loaded or injected ECM hydrogel may flow to the loading channel. The second layer may comprise a loading channel in fluid communication with one or more loadings ports for receiving the ECM hydrogel in various embodiments. Advantageously, loading of the ECM hydrogel (e.g. injection) through the loading port(s) enables easy and controlled fabrication of the ECM patterns. On the other hand, when the ECM hydrogel is loaded directly to the space defined between the first and second layers (i.e. without using loading ports), it becomes difficult to control and patterning of the ECM hydrogel becomes prone to failure.

While surface of the second layer may be patterned to define a loading channel for receiving the ECM hydrogel, the surface of the first layer may be patterned to comprise a plurality of structures having the same height in some embodiments. These plurality of structures define the geometrical configuration of the microchannel. The height of these structures may define depth of the microchannel.

Once geometrical configurations of the loading channel and microchannel have been decided, the first and second layers may be combined to form the device, i.e. form a template for patterning the ECM hydrogel. In various embodiments, the first layer may serve as the top layer and the second layer may serve as the bottom layer, such that the first layer is first aligned and positioned above the second layer, and then directly attached to the second layer with the surface of the first layer having the plurality of structures facing the loading channel. The term "combined", in this context, refers to any form of attaching the two layers together such that ECM hydrogel does not leak out from the device. In other words, the first layer may be attached over the second layer. In a non-limiting example, the first and second layers may be bonded together by plasma treatment.

When the two layers are attached, an open chamber may be defined. The open chamber may have one or more regions with reduced cross-sectional area due to the presence of the plurality of structures projecting towards and/or into the loading channel. The cross-sectional area may be one that extends throughout the length of the entire open chamber.

In the one or more regions with reduced cross-sectional area, due to surface tension arising in these narrowed regions, the ECM hydrogel supplied to the loading channel may be confined to these regions. Subsequently, when the ECM hydrogel is set (i.e. polymerized or crosslinked), a perfusable channel (as defined by the ECM hydrogel and plurality of structures of the first layer) may be formed in the open chamber. Accordingly, in some embodiments, the patterned surface of the first layer may comprise a plurality of structures having the same height extended towards the loading channel, wherein the plurality of structures having the same height and the loading channel may define one or more regions having reduced cross-sectional area which the extracellular matrix hydrogel may be confined to fill, thereby forming the perfusable channel.

The perfusable channel formed in the open chamber may be seeded with cells or transformed into vascular channels usable for various kinds of research. In various embodiments, the perfusable channel may be at least 100 μm wide. In some instances, the perfusable channel may be 100 μm to 1000 μm wide. The width of the perfusable channel may be derived from the width of the microchannel(s). When microchannel(s) less than 100 μm wide are used, the perfusable channel may not be properly formed as the ECM hydrogel tends to overflow out of their confined regions.

The perfusable channel may take on the geometrical configuration of the first layer. In some instances, the perfusable channel may comprise a T-shaped junction, a serpentine junction, a Y-shaped junction or a filleted Y-shaped junction.

In other embodiments, there is also provided a device for patterning extracellular matrix hydrogel comprising: a first layer comprising a surface patterned to define at least one microchannel; a substrate for receiving the extracellular matrix hydrogel, wherein the substrate comprises no loading channel, wherein the first layer is attached over the substrate with the patterned surface facing the substrate to define an open chamber with one or more regions having a cross-sectional area reduced by the patterned surface, and wherein the extracellular matrix hydrogel is confined to fill the one or more regions having the reduced cross-sectional area, thereby forming at least one perfusable channel in the open chamber. Certain advantages associated with the embodiments as described above may be applicable to these other embodiments, and vice versa.

These embodiments, however, differ from the earlier described embodiments in that a second layer is not used. Instead, the second layer is now replaced with a substrate having no loading channel, i.e. surface need not be patterned to form the loading channel. This circumvents the need of having to pattern two separate layers. Instead, as mentioned above, designs of the vascular microchannel and the loading channel may be solely imprinted onto a single first layer.

The substrate may be optically pervious, i.e. allow some or all light to pass through. The optically pervious substrate may be transparent or translucent. Advantageously, the optically pervious substrate improves imaging at higher magnifications with better resolutions. The optically pervious substrate may be a cover slip or a glass slide etc. The optically pervious substrate may have flat surface(s).

Other components of the present device in these embodiments may be similar to the earlier embodiments described above. The device of these embodiments may also have the first layer. The first layer may comprise or consist of PDMS, poly(methyl methacrylate), polycarbonate, glass, cyclic olefin copolymer, polystyrene or silicon. The first layer may also have a microchannel that takes on any geometrical configuration as mentioned above. For example, the microchannel may comprise a T-shaped junction, a serpentine junction, a Y-shaped junction or a filleted Y-shaped junction.

However, because the first layer may be patterned differently in these embodiments (i.e. incorporating both designs of the vascular microchannel and loading channel), more than one microchannel may be formed in the first layer. As surface of the first layer may be modified in these embodiments to incorporate both designs, the substrate may be advantageously used instead of a second imprintable (e.g. PDMS) layer.

Regarding modifications to the patterning of the first layer, the patterned surface of the first layer may, for example, comprise a plurality of depressions having different depths extending away from the substrate, wherein the plurality of depressions having different depths and the substrate may define the one or more regions having reduced cross-sectional area which the extracellular matrix hydrogel may be confined to fill, thereby forming the at least one perfusable channel.

In some other instances, the patterned surface may comprise a plurality of depressions having the same depth extending away from the substrate, wherein the plurality of depressions having the same depth and the substrate may define the one or more regions having reduced cross-sectional area which the extracellular matrix hydrogel may be confined to fill, thereby forming the at least one perfusable channel.

Despite the different patterning of the first layer, the at least one perfusable channel formed may still be at least 100 µm wide, or 100 µm to 1000 µm wide. The at least one perfusable channel may take on the geometrical configuration of the at least one microchannel of the first layer, such as comprising a T-shaped junction, a serpentine junction, a Y-shaped junction or a filleted Y-shaped junction.

In the present disclosure, there is further provided for a method of patterning extracellular matrix hydrogel, comprising: providing a device as described in any of the above embodiments; loading the extracellular matrix hydrogel into the device; and polymerizing the extracellular matrix hydrogel in one or more regions of the device having a reduced cross-sectional area to form at least one perfusable channel in an open chamber of the device. The method is advantageously versatile in that it may be used with the device as described in the above embodiments for patterning ECM hydrogel (regardless of whether the second layer or the substrate is used).

Advantages associated with various embodiments of the present device as described above may be applicable to the present method, and vice versa.

The present method is particularly capable of patterning ECM hydrogel into various geometrical configurations due to the present device used.

In some embodiments, when the present method utilizes the first layer and the substrate, alignment of the first layer and the substrate may not be needed since the patterns of the vascular microchannel and loading channel are juxtaposed during photolithography. In this regard, a two-step lithography may be advantageously used to enable creation of the loading channel and microchannel on a single layer. In various embodiments, the present method may lead to at least one microchannel formed in the first layer.

After providing the device, the method may further comprise a step of mixing a first plurality of cells with the ECM hydrogel before the loading step according to some embodiments. This is advantageous because it allows for co-culture systems to be fabricated.

The ECM hydrogel to be loaded or injected may comprise collagen, fibrin gel and/or gelatinous protein mixture secreted by Engelbreth-Holm-Swarm (EHS) mouse sarcoma cells.

In various embodiments, the step of loading the ECM hydrogel may occur at a pressure of 400 Pa to 700 Pa. The ECM hydrogel loading tends to be difficult to control at pressures below 400 Pa. Above 700 Pa, the loaded ECM hydrogel may overcome the surface tension to cause a loss of capillary burst valve effect, thereby allowing the ECM hydrogel to spread throughout the space between the first layer and the substrate, resulting in failure of ECM patterning. After the ECM hydrogel is filled and confined to the one or more regions (with reduced cross-sectional area) of the present device, a polymerizing step may be carried out for 20 mins to 40 mins at 30° C. to 45° C. As an example, at 37° C., the ECM hydrogel loaded (e.g. collagen) may form a porous gel within 30 mins. At lower temperatures, gel formation may be longer (e.g. up to 48 hours at 4° C.). Meanwhile, higher temperatures (above 45° C.) result in dehydration and shrinkage of the loaded ECM hydrogel. During polymerization, crosslinking within the ECM hydrogel may occur. Crosslinking of the ECM hydrogel tends to increase mechanical stability and leads to formation of a porous matrix that mimics in vivo cellular microenvironment.

According to various embodiments, the method may further comprise a step of seeding a second plurality of cells in the at least one perfusable channel after polymerizing the extracellular matrix hydrogel. This may be carried out when a co-culture system is required. Otherwise, the first plurality of cells as described above may not be needed.

To enhance cell growth or proliferation, the method may further comprise a step of coating the at least one perfusable channel with a cell adhesive before seeding the second plurality of cells. In some instances, the cell adhesive may be composed of the same material as the ECM hydrogel because such materials may also facilitate seeding of the cells. In some embodiments, the cell adhesive may comprise or consist of fibronectin. In various embodiments, the cell adhesive may comprise or consist of fibronectin, type I collagen, gelatin or gelatinous protein mixture secreted by Engelbreth-Holm-Swarm (EHS) mouse sarcoma cells.

While the methods described above are illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

EXAMPLES

The present disclosure relates to a device used in a method, and the method itself, for rapid 3D patterning of extracellular matrix (ECM) hydrogel for microfluidic vascular studies. The present device and method, and their uses, are described in the examples below.

Example 1a: Device Design

Figure 1A:
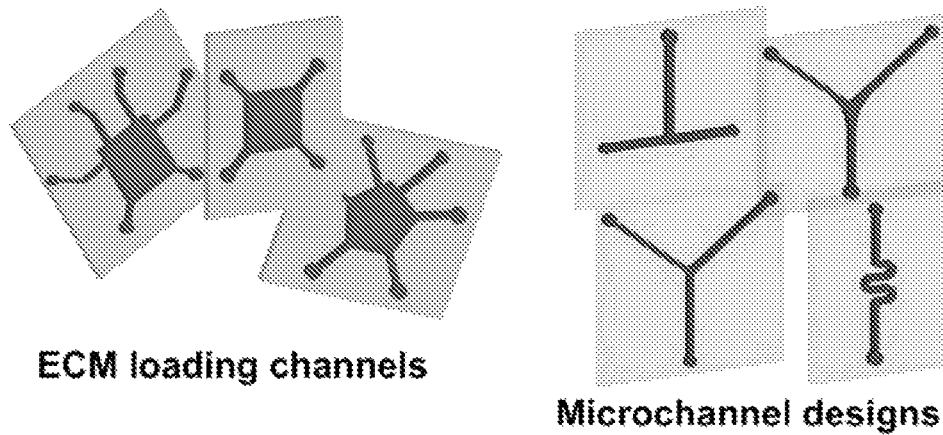
Figure 2:
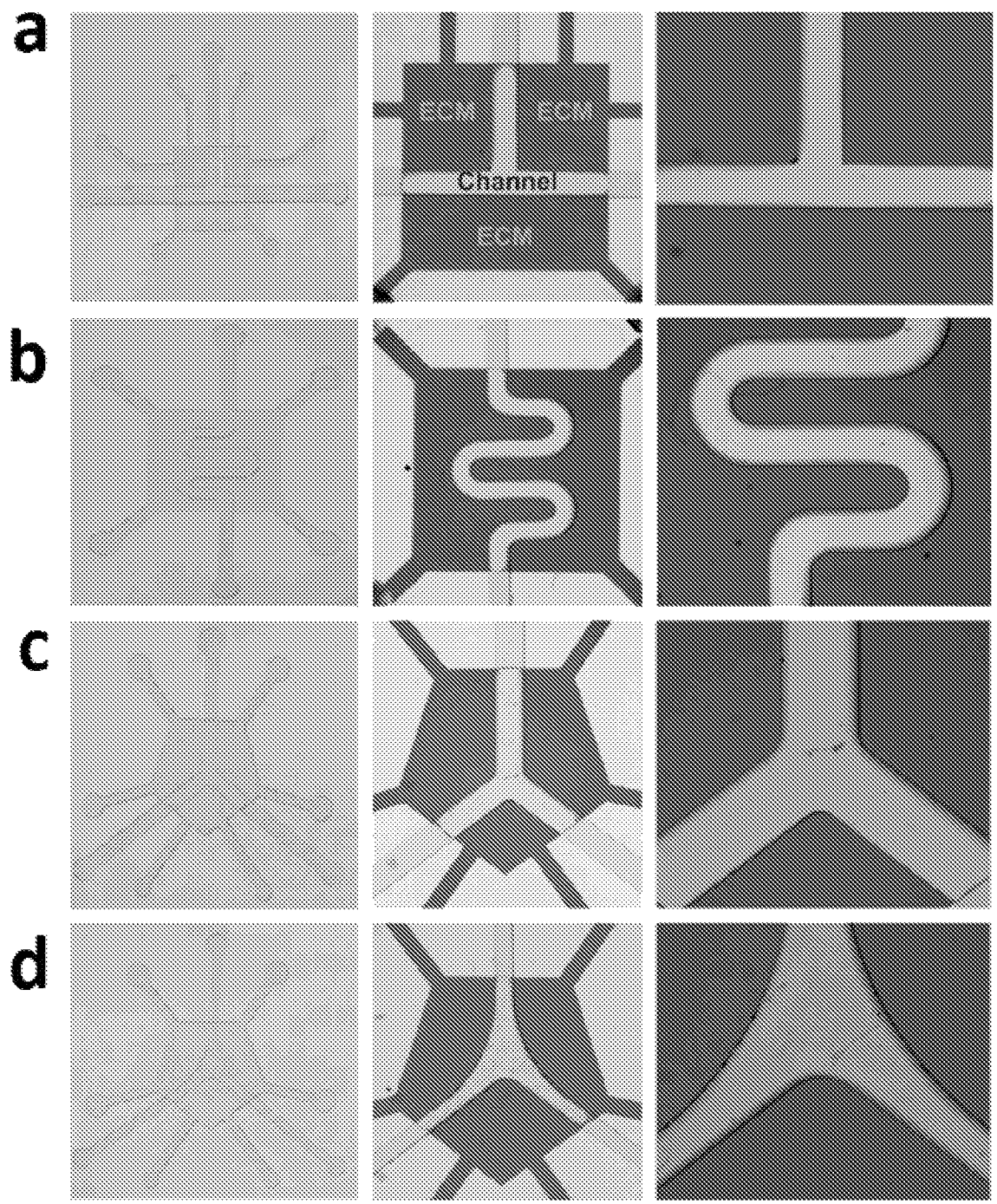
Figure 3:
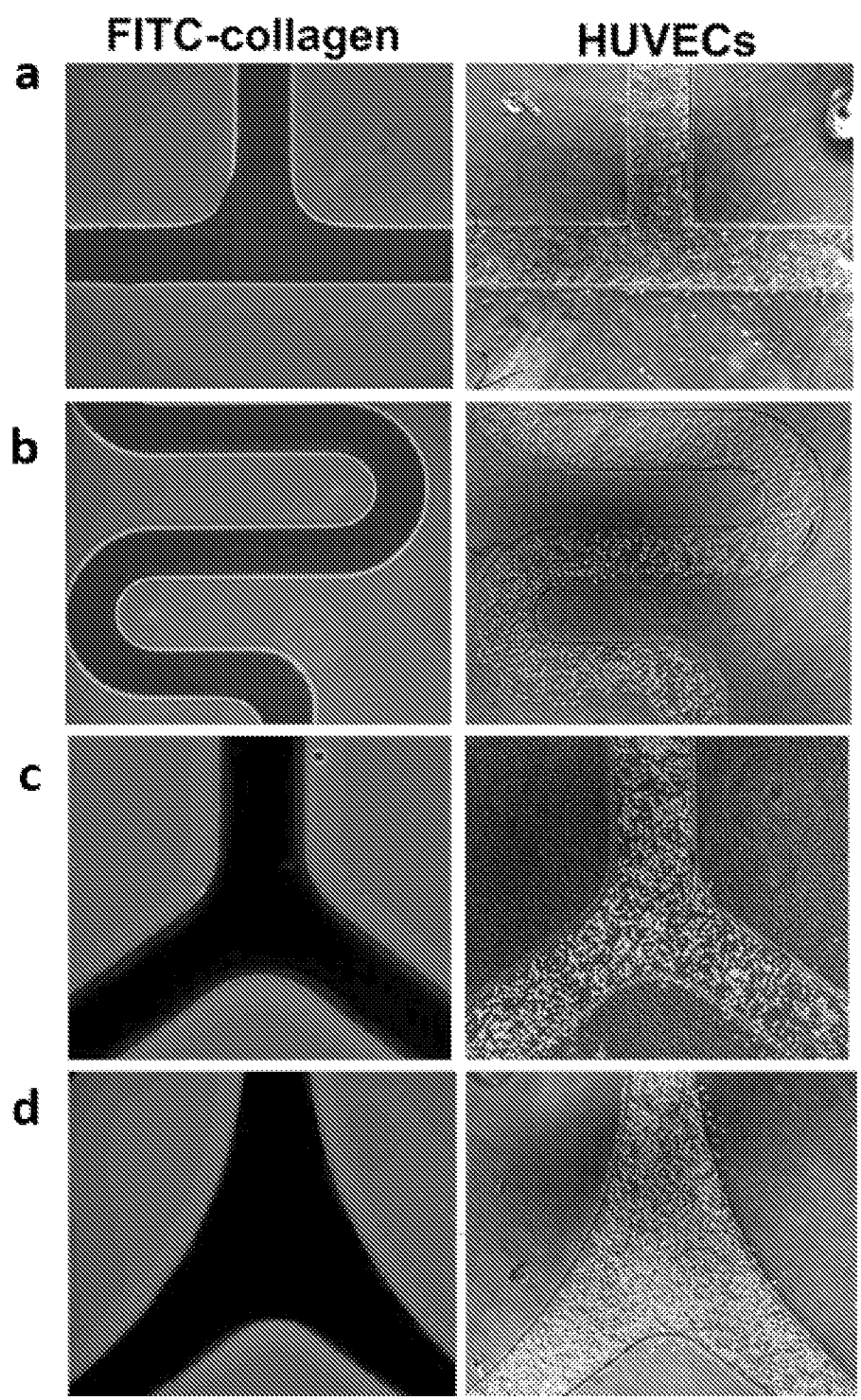
FIG. 3a shows images of a perfusable channel patterned using type I collagen and seeded with vascular cells (HUVECs). Specifically, the left fluorescence image of FIG. 3a indicates well defined ECM hydrogel walls using FITC-collagen (2.5 mg/ml; where FITC represents fluorescein isothiocyanate) for a perfusable channel with T-junction. Right image of FIG. 3a shows HUVECs seeded into the patterned perfusable channel having a T-junction with minimal crossover into the collagen walls.
FIG. 3b shows images of a perfusable channel patterned using type I collagen and seeded with HUVECs. Specifically, the left fluorescence image of FIG. 3b indicates well defined ECM hydrogel walls using FITC-collagen (2.5 mg/ml) for a perfusable channel with serpentine. Right image of FIG. 3b shows HUVECs seeded into the patterned perfusable channel having a serpentine with minimal crossover into the collagen walls.
FIG. 3c shows images of a perfusable channel patterned using type I collagen and seeded with HUVECs. Specifically, the left fluorescence image of FIG. 3c indicates well defined ECM hydrogel walls using FITC-collagen (2.5 mg/ml) for a perfusable channel with Y-junction. Right image of FIG. 3c shows HUVECs seeded into the patterned perfusable channel having a Y-junction with minimal crossover into the collagen walls.
FIG. 3d shows images of a perfusable channel patterned using type I collagen and seeded with HUVECs. Specifically, the left fluorescence image of FIG. 3d indicates well defined ECM hydrogel walls using FITC-collagen (2.5 mg/ml) for a perfusable channel with filleted Y-junction. Right image of FIG. 3d shows HUVECs seeded into the patterned perfusable channel having a filleted Y-junction with minimal crossover into the collagen walls.

The 2-layer polydimethylsiloxane (PDMS) device consists of an ECM hydrogel loading channel (bottom), and a vascular microchannel design (top) which acts as a template for ECM patterning (FIG. 1a). Each ECM loading channel may be designed with multiple pairs of gel loading ports (inlet and outlet), and the design complexity depends on the number of ECM walls required to form the resultant perfusable channel. For example, a straight or serpentine perfusable channel needs 2 ECM regions to define the shape, and has 2 pairs of gel loading ports (one on each channel side). Similarly, a T-junction or Y-channel requires 3 ECM regions and may have 3 pairs of gel loading ports (see FIG. 2c).

Figure 1B:
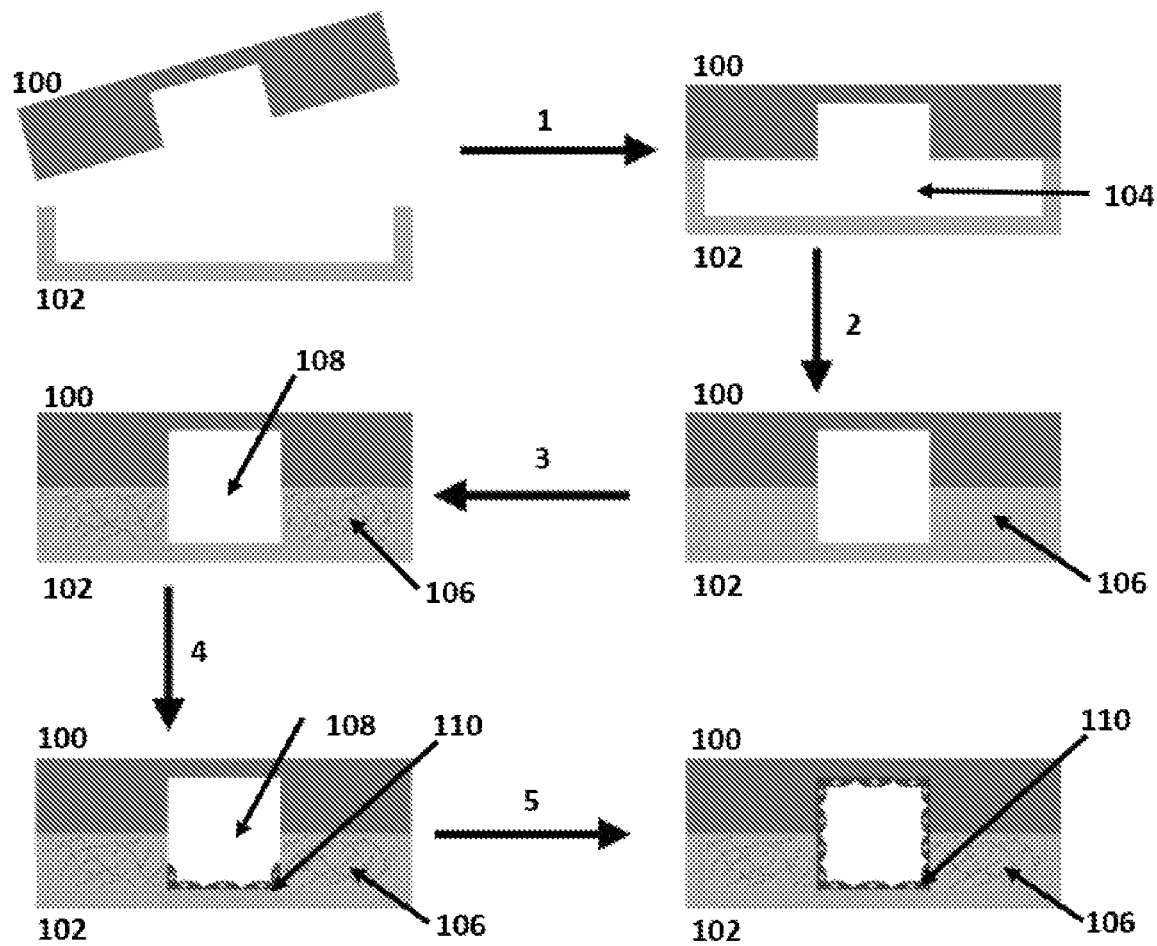
FIG. 1b is a schematic illustration of the ECM hydrogel loading procedure. The ECM loading channel (bottom layer) and vascular microchannel design (top layer) are aligned and bonded together after plasma treatment. The ECM hydrogel is loaded through the bottom ports, which then flows and stops at the boundaries defined by the microchannel of the top layer due to surface tension. After incubation for 30 minutes (mins) at 37° C., the ECM hydrogel is polymerized to form a perfusable channel, and vascular cells are then seeded into the perfusable channel for cell culture.

A schematic illustration of ECM hydrogel loading/patterning is depicted in FIG. 1b. The microchannel design top template (first layer) 100 is aligned and attached over the bottom ECM loading channel (second layer) 102 by plasma bonding/treatment 1. This forms an open chamber 104 with one or more regions having reduced a cross-sectional area. Upon ECM hydrogel loading 2, the open chamber (i.e. the reduced cross-sectional areas) confines the loaded ECM hydrogel 106 to the one or more regions with reduced cross-sectional area in the open chamber due to surface tension. Accordingly, the loaded ECM hydrogel 106 only fills up the regions with reduced cross-section. Thereafter, the loaded ECM hydrogel 106 is incubated at 37° C. for about 30 minutes (mins) (which also serves as the polymerizing step 3 for polymerization of the ECM hydrogel) to form a perfusable channel 108. Vascular cells 110 are then seeded 4 in the perfusable channel 108 and cultured 5 for 2 to 4 days.

In summary, the microfabricated ECM loading channel (e.g. depth 150 µm) and vascular microchannel design (e.g. depth 150 µm) are aligned and bonded together using plasma treatment. The microchannel design (top layer) defines the boundaries of where the ECM hydrogel is confined due to the surface tension, to form perfusable channels bounded by ECM sidewalls. After the ECM hydrogel has polymerized, vascular cells are seeded into the perfusable channel and grown to confluency for about 2 to 4 days. FIG. 2a to FIG. 2d show the aligned ECM loading channels with microchannel design template of different geometries. As proof-of-concept, type I collagen (2.5 mg/ml) was used to form T-junction, serpentine, Y-junction and filleted Y-junction perfusable channels (e.g. channel width 500 µm).

Using the method described in this example, the cross-linked (or polymerized) ECM walls were well defined as evidenced by the use of FITC-collagen (see FIG. 3a to FIG. 3d; where FITC represents fluorescein isothiocyanate). Vascular cells (HUVECs) were seeded into the perfusable channel for static in vitro cell culture, and flow perfusion can also be established in the system if required.

Example 1b: Device Preparation

Preparation of the top vascular microchannel design template and the bottom ECM loading channel template are described as follows.

A two-layered polydimethylsiloxane (PDMS, Dow Corning) blood vessel on-a-chip model was fabricated using standard photolithography and soft lithography procedures. Briefly, the PDMS prepolymer was mixed with the curing agent in a 10:1 ratio (w/w) and poured on a patterned silicon wafer template. The mixture was cured in an oven at 80° C. for 2 hours and peeled carefully from the wafer. Inlet holes (1.5 mm) were defined using a biopsy puncher on the top layer. The alignment of the PDMS layers resulted in the formation of a differential height (channel expansion), with the channel intersection having a combined height or depth of 300 µm. The height was measured from the cross-sectional slice of each PDMS layer using an optical microscope.

Example 2: Diffusion Effects in Patterned ECM Hydrogel

Figure 4:
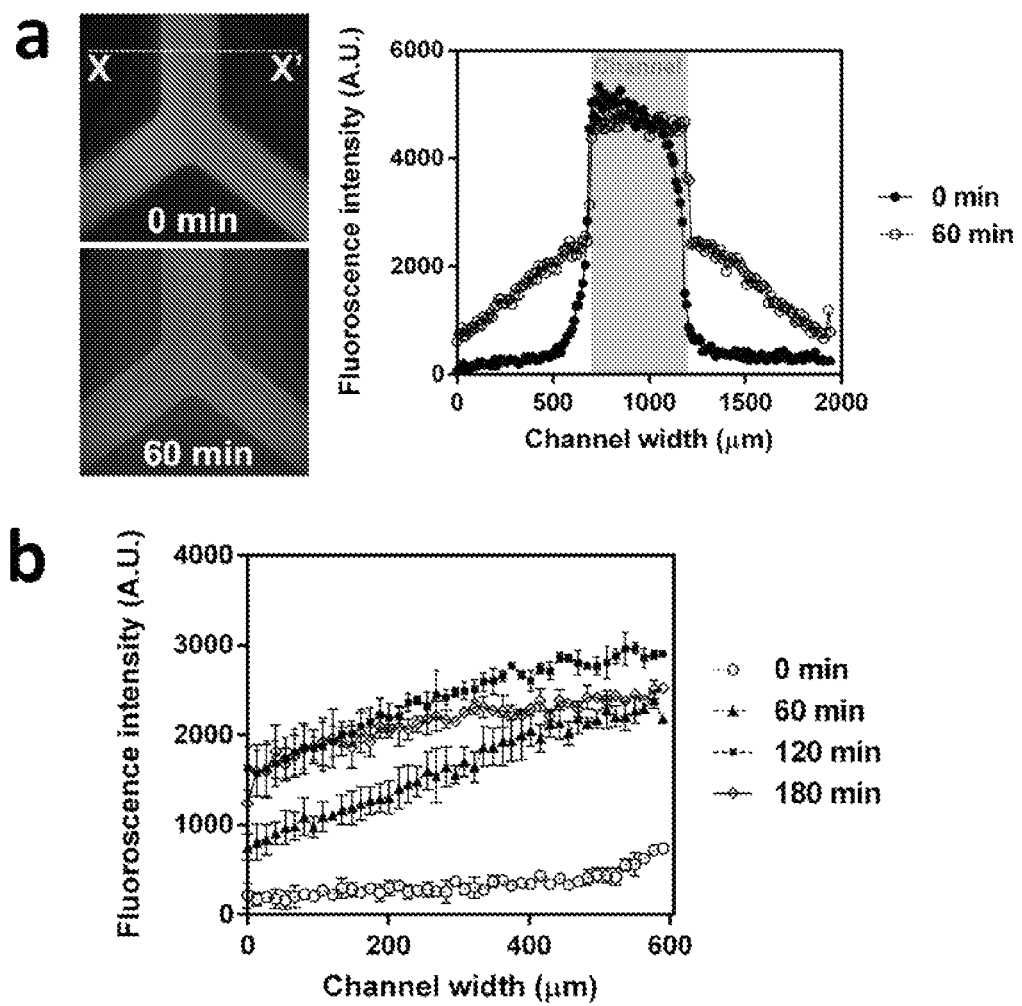
FIG. 4a demonstrates stable diffusion gradient of biomolecules within the ECM hydrogel. Specifically, the left images of FIG. 4a show FITC-dextran (40 kDa) loaded into a collagen-patterned perfusable channel having a Y-shaped junction (500 μm wide). Fluorescence intensity linescan across the perfusable channel (X-X') indicates stable diffusion of biomolecules after 60 mins. The highlighted region in the right image of FIG. 4a corresponds to the perfusable channel position.
FIG. 4b shows stable diffusion gradient of biomolecules within the ECM. Specifically.

To mimic physiological microenvironment, FITC-Dextran (40 kDa) was introduced into a Y-channel to study diffusion effects in the ECM region proximal to the microchannel. Stable diffusion gradient was established within the first hour, and was maintained for long term cell culture (FIG. 4a and FIG. 4b). This indicates the ability to seed other vascular-related cell types including smooth muscle cells, fibroblasts and pericytes within the ECM hydrogel to create co-culture systems. Cell-cell communication is established by diffusion of biomolecules through the porous ECM, and cell-cell interactions (cell migration, angiogenesis) can be visualized directly inside the ECM.

Example 3: Development of Vessel Network in Patterned ECM Hydrogel

In this example, to demonstrate well developed vessel network in the patterned ECM microdevice, HUVECs were cultured in the perfusable channel for 2 to 4 days to form confluent monolayer at the channel bottom. Confocal imaging was performed to confirm the presence of HUVECs monolayer along the ECM sidewalls (FIG. 5a and FIG. 5b). This is important for study of endothelial barrier functionalities including barrier permeability and leukocyte transmigration through the endothelial monolayer.

Example 4: Effect of Microchannel's Dimension and Hydrogel Type

The method of ECM patterning is advantageously based on surface tension driven capillary burst valves (CBV) effect. CBV is a fluid dynamic phenomenon which results in pinning of flowing liquid at a microchannel expansion. The present method is unique in that it utilizes CBV along the z-axis (vertical), instead of channel expansions in the x-y plane (horizontal), to achieve patterning of a continuous ECM wall. The patterning resolution in the present method is first characterized using microchannels of different dimensions.

FITC loaded collagen was introduced into the devices with different microchannel width (FIG. 6a). Reproducibility was excellent for larger channel widths (200 µm, 500 µm and 1000 µm with constant channel height or depth of 150 µm). However, for channel width of 100 µm, the collagen gel tends to seal the perfusable channel, if not careful during loading, by bulging over from both sides (regions where cross-section of the open chamber are reduced). Hence, the lower limit for ECM patterning using this method was taken as 100 µm. The use of the term "height" or "depth", in the present disclosure, depends on whether the measurement refers to height of structures defining the channel or how deep the channel is. For example, if the dimension is defined with respect to the structures, then "height" may be used. If the dimension is defined with respect to depression, then "depth" may be used.

Characterization of microchannels with different heights or depths (25 µm, 50 µm and 150 µm at a constant channel width of 500 µm) to study the impact of microchannel height or depth on successful ECM patterning was also carried out. To visualize this, the chip was sliced along the x-axis (X-X') and bonded the channel cross-section on a cover slip. As observed (FIG. 6b), ECM patterning was independent of the microchannel height or depth in the top layer (i.e. first layer).

Two parameters were further defined (see FIG. 6c). They are the maximum gel distance, D, at the centre of the bulge (from the edge of the top microchannel) and the gel distance, d, along the bottom surface. It was observed that as the applied gel loading pressure increased ($P_a$), the bulging distances (D and d) increased while the gel remained pinned at the top surface (FIG. 6c). In addition, the bulging distance exhibited a strong linearity with the contact angle with the top surface which was consistent with Young-Laplace equation. A maximum value of about 50 µm for D was also observed. This was similar to earlier observations and corresponded to a minimum channel width of about 100 µm (FIG. 6c).

Lastly, it was demonstrated that the present method is independent of the hydrogel type by successfully patterning devices with other commonly used ECMs such as fibrin (i.e. fibrin gel) and gelatinous protein mixture secreted by Engelbreth-Holm-Swarm (EHS) mouse sarcoma cells (i.e. Matrigel) (see FIG. 7).

Example 5: Blood-Vessel-On-A-Chip Using Present Method and Device

To demonstrate a well developed vessel network in the patterned ECM microdevice, HUVECs were cultured in the perfusable channel for about 2 to 3 days to form confluent monolayer throughout the channel in 3-dimensions. Confocal imaging was performed to confirm the formation of an intact and continuous HUVECs monolayer along the ECM sidewalls (FIG. 8). This is critical as, in vivo, an intact endothelial barrier is necessary to perform key functionalities such as size selective diffusion of molecules into tissues and maintenance of homeostasis.

Once a confluent HUVECs monolayer was created, FITC-conjugated dextran (40 kDa and 10 kDa) was loaded into the perfusable channel to test the HUVECs barrier permeability under static conditions (see FIG. 9a). The effective barrier permeability (EP) was calculated from the fluorescence intensity of FITC-dextran after 1 hour using Fick's law, as represented by the equation below.

$$EP = \frac{W}{T} \times \frac{I_{60} - I_0}{I_0 - I_b}$$

Where $I_b$ is the background intensity at the start, $I_0$ is mean fluorescence intensity of a specific portion at the start, $I_{60}$ is the mean fluorescence intensity at the same portion after 1 hour, W is the width of the channel (i.e. perfusable channel after ECM loading) in centimetres and T is total time in seconds.

As expected, FITC-dextran diffused in a size selective manner with greater diffusion of the smaller molecules (see FIG. 9b). Moreover, these values of effective barrier permeability ($6.93 \times 10^{-6}$ cm/s for 10 kDa dextran versus $3.014 \times 10^{-6}$ cm/s for 40 kDa dextran, p<0.01) matched with reported results.

Further, the present method and device were used to study inflammation induced vascular leakiness by treating the vasculature using tumor necrosis factor alpha (TNF-α, 10 ng/m), a potent inflammatory marker. A significant modulation in vessel leakiness was observed due to inflammation in comparison to healthy vasculature ($3.014 \times 10^{-6}$ cm/s for healthy EC vs. $7.9 \times 10^{-6}$ cm/s for inflamed EC, p<0.01) (see FIG. 9c).

Integrity of the vasculature under flow was also assessed by perfusing fluorescently tagged 2 μm beads at a wall shear stress of 3 dyne $cm^{-2}$ (0.3 Pa) (see FIG. 9d). Similar to the dextran diffusion assay, a significant increase (about 2 fold) in beads penetration was observed due to inflammation (see FIG. 9e). Such leaky vessels are vital in pathologies such as cancer and atherosclerosis.

Characterization of full width at half maximum (FWHM) of the fluorescent spectrum for healthy and TNF-α treated EC (n=4) are shown in FIG. 9f.

The above results highlight that the present model and device are useful in developing microfluidic models for studying pathological conditions in static and perfusion cultures.

Example 6a: Using Present Method and Device for Study of Chemotaxis

Neutrophil transendothelial migration (chemotaxis) is a physiological process where the neutrophils migrate to the site of infection as part of the body's innate immune response. This key process is replicated to further elucidate the physiological relevance of the present vasculature model.

A chemoattractant, N-formylmethionine-leucyl-phenylalanine (fMLP, 500 nM) was introduced into the gel ports of the ECM chamber and allowed to diffuse through the collagen gel towards the perfusable channel. FITC dye was added with the fMLP to visualize the gradient. A stable gradient was generated over a period of 8 hours (see FIG. 10a and FIG. 10b). Neutrophils from whole blood were purified using Dean Flow Fractionation and introduced into the endothelialized vasculature, 2 hours after the introduction of fMLP into the ECM ports. HUVECs in the perfusable channel were inflamed using TNF-α to enhance their interactions with the neutrophils. In the presence of fMLP, neutrophils migrated through the leaky HUVEC monolayer and into the collagen in the direction of increasing concentration of the chemoattractant (FIG. 10c). Neutrophil migration was monitored in real time for 4 hours and significant neutrophil migration was observed due to the fMLP gradient (FIG. 10d). With increasing evidence of neutrophil or immune cell dysfunction as a marker for risk assessment, especially in disorders such as diabetes, such a model proves useful in profiling neutrophil and other blood cell functionalities in diseases studies.

Example 6b: Co-Culturing of Smooth Muscle Cells (SMCs) and HUVECs

In this example, perivascular cells were cultured in 3D, inside the ECM surrounding the vasculature. Aortic smooth muscle cells (SMCs, Lonza) were mixed with the collagen and introduced into the chip following which the ECs were cultured inside the perfusable channel to confluency. The cells were cultured for 3 days and confocal imaging was performed to visualize the 3D orientation of the perivasculature around the endothelialized perfusable channel (FIG. 11a). Prior studies have demonstrated the role of perivasculature in the maintenance of vessel integrity.

Vessel integrity of the HUVEC monolayer in the presence of SMCs under inflammation were then analyzed. Observably, the presence of SMCs lowered the diffusive permeability of inflamed HUVEC monolayer to 40 kDa dextran (FIG. 11b).

To further validate these results, SMCs were cultured in one portion of the chip while the other section was without SMCs (FIG. 11c). The barrier permeability of these systems were tested under inflammation. In agreement with the earlier observation, the section without SMCs was leakier (FIG. 11d). These results signify the flexibility of the present method and device for developing microfluidic vasculature model used in creating co-culture systems with multiple cell types which is necessary for creating different organ-on-a-chip models to study organ functionalities and for drug testing.

Example 7: 3D Biomimetic Model for Cardiovascular Diseases Using Present Method and Device After extensive characterization of the ECM patterning technique, the present method is applied to develop stenosed microvasculature models to mimic an atherosclerotic plaque (FIG. 12a). Stenosis (narrowing) of blood vessel is a critical step in atherosclerosis progression resulting in blood flow abnormalities and shear induced endothelial dysfunction. The present ECM patterning technique can be used to create different channel constrictions by altering the microchannel design. The significance of the developed stenosis channel was illustrated by comparing the perfusion of FITC-conjugated 2 μm beads through an 80% constricted perfusable channel with constrictions made of PDMS and collagen at an inlet wall shear stress of 10 dyne cm$^{-2}$ (1 Pa). No beads accumulation was observed on the PDMS constriction while a significant number of beads accumulated on the proximal edge of the collagen patterned channel (FIG. 12b). This was possibly due to the convective flow through the porous collagen gel on the proximal side of the constriction facilitating enhanced bead contact with the gel. The channel constrictions were varied for the same experiment but beads accumulation was not observed for other channel constrictions (FIG. 12c), indicating the significance of channel geometries for atherosclerotic studies.

Example 8: Whole Blood Perfusion Studies Using Present Method and Device

In this example, human whole blood (3 times diluted with saline to maintain ECM integrity) was perfused through the collagen stenosed chip (FIG. 13a). First, the whole blood was perfused through the perfusable channel in the absence of HUVECs to eliminate the influence of cellular interactions and to understand the influence of collagen-stenosis induced flow disturbance on the blood cells. No cell adhesion was observed in regions upstream nor downstream from the constriction, though at the proximal edge of the constriction, significant platelet accumulation was observed (FIG. 13b). Moreover, increased accumulation of platelets was observed for 80% constriction in comparison to 50% constriction. This effect could be attributed to the increased shear induced activation of platelets due to 80% channel constriction in comparison to 50% constriction.

Next, whole blood was perfused at 1 dyne cm$^{-2}$ (0.1 Pa) through the endothelialized 80% collagen constricted perfusable channel. Minimal leukocyte adhesion was observed over healthy endothelium after 15 mins. Shear activation, however, resulted in platelet adhesion to the endothelium around the constriction (FIG. 14a). In contrast, whole blood perfusion at 1 dyne cm$^{-2}$ (0.1 Pa) for 15 mins over inflamed (TNF-α) endothelium increased leukocyte-endothelium interactions (rolling and adhesion). However, when the flow rate was increased to 10 dyne cm$^{-2}$ (1 Pa), leukocyte-endothelium interactions decreases, while a corresponding increase in platelet adhesion at the proximal and distal edges of the constriction was noted (FIG. 14c and FIG. 14d). Similar to 2 μm beads accumulation at the proximal edge of the constriction, significant accumulation of platelets was observed. This reinforces the hypothesis of the presence of a convective flow along the porous collagen constriction. Considering the above results, the robustness of the present ECM patterned model to support whole blood perfusion experiments, which is significant in liquid biopsies, is demonstrated. Such an atherosclerotic model can also be used as a disease model to study the progression of atherosclerosis, monocyte-endothelium interaction and platform for drug testing and personalized care.

Example 9: Further Modification of Present Method and Device

A further modification of the above fabrication procedure (two-layered polydimethylsiloxane (PDMS) chips) is to utilize a two-step photolithography to create differential heights or depths necessary for the capillary burst valve (CBV) effect [see FIG. 15a (present method) and FIG. 15b (modified method)].

To make the microfluidic chips via the present method illustrated in FIG. 15a, the patterned PDMS top layer (first layer) needs to be bonded to a substrate, which would be the bottom PDMS layer (second layer) in this instance. In this first approach, the bottom PDMS layer (with the ECM loading channel design) acts as the substrate. Upon bonding the two layers of PDMS, the imprinted channel designs define structures having a plurality of heights necessary to give rise to surface tension due to the CBV effect.

In the other approach using a first PDMS layer (top layer) and a flat substrate, the first PDMS layer was fabricated using a 2-step lithography to create both the vascular microchannel and hydrogel loading channel designs on the same silicon wafer so that the different designs were imprinted together onto a single layer of PDMS. Hence, a flat substrate, such as a glass slide, can be used to complete this chip.

Briefly, for the latter approach, silicon wafer was spin-coated with the photoresist (SU-8, Microchem) and exposed to ultraviolet (UV) radiation (365 nm) to prepare the mold for the ECM chamber. Next, another layer of the photoresist was spin-coated on the same Si wafer (over the ECM chamber design) and the microchannel design was aligned and exposed to UV radiation, thereby creating a patterned mold with differential heights/depths. Finally, soft lithography was used to fabricate the PDMS devices, and the chips were completed by bonding them to an optically pervious substrate, including but not limited to, cover slip(s) or glass slide(s).

This modification is advantageous because the differential height(s)/depth(s) can arise from (1) one or more created depression(s) having the same or different depth(s) extending away from the substrate, or (2) as one or more structures with same or different heights extending towards the substrate. Apart from this, the modification is also easier to handle and has the further advantages as follows: (1) unlike the above method, no alignment is required since the ECM loading channel and the microchannel are juxtaposed during photolithography, the PDMS chips can be bonded directly on cover slip(s) or glass slide(s) without the need for alignment, and (2) use of cover slip(s) or glass slide(s) as the base of the PDMS chip improves imaging at higher magnifications with better resolutions.

As proof of concept for the modified fabrication procedure, two chip configurations were created; chip with hydrogel channel at the centre, and chip with hydrogel channel at the sides (FIG. 16a). The ability of these chips to create hydrogel patterns were tested by loading collagen hydrogel laden with FITC dye into the respective channels (FIG. 16b).

Example 10: Commercial Applications

The technology development of a rapid ECM hydrogel patterning strategy in microfluidic devices is of great commercial interest with numerous biomedical applications ranging from tissue engineering to drug discovery. Accordingly, the present method and fabricated device are flexibly applicable for different hydrogels (collagen, matrigel, fibrin etc.), and can be used to create endothelialized in vitro vascular model(s) of different geometries for studying endothelial functions in cancer (angiogenesis), diabetes/cardiovascular diseases (vasculogenesis) and blood-brain barrier (barrier permeability). With the simplicity in hydrogel patterning and flexibility to create any vascular geometry presented by the method and device disclosed herein, it is envisaged that such a method and device have a significant impact on "organ-on-a-chip" and vascular-related research.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A device for patterning an extracellular matrix hydrogel comprising:
   a first layer comprising a patterned surface to define a microchannel;
   a second layer comprising a loading channel in fluid communication with one or more loading ports for receiving the extracellular matrix hydrogel;
   wherein the first layer is attached over the second layer with the patterned surface facing the loading channel to define an open chamber with one or more regions having a cross-sectional area reduced by the patterned surface, and
   wherein the one or more regions having the reduced cross-sectional area are configured to confine the extracellular matrix hydrogel to each of the one or more regions having the reduced cross-sectional area, thereby forming a perfusable channel in the open chamber, wherein the perfusable channel is vertically longer than all of the one or more regions having the reduced cross-sectional area.

2. The device according to claim 1, wherein both the first layer and the second layer comprise polydimethylsiloxane, poly(methyl methacrylate), polycarbonate, glass, cyclic olefin copolymer, polystyrene, or silicon.

3. The device according to claim 1, wherein the microchannel comprises a T-shaped junction, a serpentine junction, a Y-shaped junction, or a filleted Y-shaped junction.

4. The device according to claim 1, wherein the patterned surface comprises a plurality of structures having the same height extended towards the loading channel, wherein the plurality of structures having the same height and the loading channel define the one or more regions having reduced cross-sectional area which the extracellular matrix hydrogel is confined to fill, thereby forming the perfusable channel.

5. The device according to claim 1, wherein the perfusable channel is at least 100 μm wide.

6. The device according to claim 1, wherein the perfusable channel comprises a T-shaped junction, a serpentine junction, a Y-shaped junction, or a filleted Y-shaped junction.

7. A method of patterning an extracellular matrix hydrogel, the method comprising:
   providing a device of claim 1 for patterning the extracellular matrix hydrogel, the device comprising:
      a first layer comprising a patterned surface to define a microchannel;
      a second layer comprising a loading channel in fluid communication with one or more loading ports for receiving the extracellular matrix hydrogel;
      wherein the first layer is attached over the second layer with the patterned surface facing the loading channel to define an open chamber with one or more regions having a cross-sectional area reduced by the patterned surface;
   loading the extracellular matrix hydrogel into the device; and
   polymerizing the extracellular matrix hydrogel in the one or more regions of the device having the reduced cross-sectional area to form a perfusable channel in the open chamber of the device, wherein the perfusable channel is vertically longer than all of the one or more regions having the reduced cross-sectional area.

8. The method according to claim 7, further comprising mixing a first plurality of cells with the extracellular matrix hydrogel before the loading.

9. The method according to claim 7, wherein the loading occurs at a pressure of 400 Pa to 700 Pa.

10. The method according to claim 7, wherein the polymerizing occurs for 20 mins to 40 mins at 30° C. to 45° C.

11. The method according to claim 7, further comprising seeding a second plurality of cells in the perfusable channel after polymerizing the extracellular matrix hydrogel.

12. The method according to claim 11, further coating the perfusable channel with a cell adhesive before seeding the second plurality of cells, wherein the cell adhesive comprises fibronectin, type I collagen, gelatin or gelatinous protein mixture secreted by Engelbreth-Holm-Swarm (EHS) mouse sarcoma cells.

13. A device for patterning an extracellular matrix hydrogel comprising:
   a first layer comprising a patterned surface to define at least one microchannel;
   a substrate for receiving the extracellular matrix hydrogel, wherein the substrate comprises no loading channel;
   wherein the first layer is attached over the substrate with the patterned surface facing the substrate to define an open chamber with one or more regions having a cross-sectional area reduced by the patterned surface, and
   wherein the one or more regions having the reduced cross-sectional area are configured to confine the extracellular matrix hydrogel to each of the one or more regions having the reduced cross-sectional area, thereby forming at least one perfusable channel in the open chamber, wherein the at least one perfusable channel is vertically longer than all of the one or more regions having the reduced cross-sectional area.

14. The device according to claim 13, wherein the first layer comprises polydimethylsiloxane, poly(methyl methacrylate), polycarbonate, glass, cyclic olefin copolymer, polystyrene, or silicon.

15. The device according to claim 13, wherein the at least one microchannel comprises a T-shaped junction, a serpentine junction, a Y-shaped junction, or a filleted Y-shaped junction.

16. The device according to claim 13, wherein the patterned surface comprises a plurality of depressions having different depths extending away from the substrate, wherein the plurality of depressions having different depths and the substrate define the one or more regions having reduced cross-sectional area which the extracellular matrix hydrogel is confined to fill, thereby forming the at least one perfusable channel.

17. The device according to claim 13, wherein the patterned surface comprises a plurality of depressions having the same depth extending away from the substrate, wherein the plurality of depressions having the same depth and the substrate define the one or more regions having reduced cross-sectional area which the extracellular matrix hydrogel is confined to fill, thereby forming the at least one perfusable channel.

18. The device according to claim 13, wherein the at least one perfusable channel is at least 100 μm wide.

19. The device according to claim 13, wherein the at least one perfusable channel comprises a T-shaped junction, a serpentine junction, a Y-shaped junction, or a filleted Y-shaped junction.

20. A method of patterning an extracellular matrix hydrogel, the method comprising:
  providing a device of claim 13 for patterning the extracellular matrix hydrogel, the device comprising:
    a first layer comprising a patterned surface to define at least one microchannel;
    a substrate for receiving the extracellular matrix hydrogel, wherein the substrate comprises no loading channel;
    wherein the first layer is attached over the substrate with the patterned surface facing the substrate to define an open chamber with one or more regions having a cross-sectional area reduced by the patterned surface;
  loading the extracellular matrix hydrogel into the device; and
  polymerizing the extracellular matrix hydrogel in the one or more regions of the device having the reduced cross-sectional area to form at least one perfusable channel in the open chamber of the device, wherein the at least one perfusable channel is vertically longer than all of the one or more regions having the reduced cross-sectional area.

* * * * *